US011197872B2

(12) United States Patent
Lisanti et al.

(10) Patent No.: US 11,197,872 B2
(45) Date of Patent: Dec. 14, 2021

(54) VITAMIN C AND DOXYCYCLINE: A SYNTHETIC LETHAL COMBINATION THERAPY FOR ERADICATING CANCER STEM CELLS (CSCS)

(71) Applicant: LUNELLA BIOTECH, INC., Ottawa (CA)

(72) Inventors: Michael P. Lisanti, Fulton, MD (US); Federica Sotgia, Fulton, MD (US)

(73) Assignee: LUNELLA BIOTECH, INC., Ontario (CA)

( * ) Notice: Subject to any disclaimer, the term of this patent is extended or adjusted under 35 U.S.C. 154(b) by 0 days.

(21) Appl. No.: 16/606,485

(22) PCT Filed: Apr. 20, 2018

(86) PCT No.: PCT/US2018/028587
§ 371 (c)(1),
(2) Date: Oct. 18, 2019

(87) PCT Pub. No.: WO2018/195434
PCT Pub. Date: Oct. 25, 2018

(65) Prior Publication Data
US 2020/0061086 A1 Feb. 27, 2020

Related U.S. Application Data

(60) Provisional application No. 62/488,489, filed on Apr. 21, 2017.

(51) Int. Cl.
| *A61K 31/65* | (2006.01) |
| *A61K 31/375* | (2006.01) |
| *A61K 31/341* | (2006.01) |
| *A61K 31/36* | (2006.01) |
| *A61K 31/47* | (2006.01) |
| *A61K 31/7004* | (2006.01) |
| *A61K 31/7048* | (2006.01) |

(52) U.S. Cl.
CPC ............ *A61K 31/65* (2013.01); *A61K 31/341* (2013.01); *A61K 31/36* (2013.01); *A61K 31/375* (2013.01); *A61K 31/47* (2013.01); *A61K 31/7004* (2013.01); *A61K 31/7048* (2013.01)

(58) Field of Classification Search
CPC .... A61K 31/65; A61K 31/655; A61K 31/375; A61K 31/36; A61K 31/7004; A61K 31/7048; A61P 35/00–04
See application file for complete search history.

(56) References Cited

U.S. PATENT DOCUMENTS

| 3,517,067 A | 6/1970 | Stern |
| 3,957,980 A * | 5/1976 | Noseworthy ........ A61K 9/0019 |
| | | 514/152 |
| 5,168,057 A | 12/1992 | Oh et al. |
| 5,250,518 A | 10/1993 | Kobrehel et al. |
| 5,441,939 A | 8/1995 | Yang |
| 5,795,871 A | 8/1998 | Narita et al. |
| 5,837,696 A | 11/1998 | Golub et al. |
| 6,043,226 A | 3/2000 | Lundy et al. |
| 6,165,999 A | 12/2000 | Vu |
| 6,475,518 B1 | 11/2002 | Baumgart et al. |
| 6,858,598 B1 | 2/2005 | McKearn et al. |
| 7,405,227 B2 | 7/2008 | Kun et al. |
| 7,485,298 B2 | 2/2009 | Powell |
| 8,075,902 B2 | 12/2011 | Powell |
| 8,357,723 B2 | 1/2013 | Satyam |
| 8,741,853 B2 | 6/2014 | Steliou |
| 9,394,233 B2 | 7/2016 | Merino et al. |
| 9,622,982 B2 | 4/2017 | Bannister et al. |
| 9,675,578 B2 | 6/2017 | Desai et al. |
| 9,801,922 B2 | 10/2017 | Spitz et al. |
| 2001/0002404 A1 | 5/2001 | Webb |
| 2005/0002942 A1 | 1/2005 | Vlahov et al. |
| 2005/0209292 A1 | 9/2005 | Chuang et al. |
| 2005/0256081 A1 | 11/2005 | Peyman |
| 2007/0048296 A1 | 3/2007 | Kajander et al. |
| 2007/0105937 A1 | 5/2007 | Pappolla et al. |
| 2008/0045589 A1 | 2/2008 | Kelley |
| 2008/0160007 A1 | 7/2008 | Powell |
| 2008/0241959 A1 | 10/2008 | Culic et al. |
| 2009/0311249 A1 | 12/2009 | Gianni et al. |
| 2010/0120679 A1 | 5/2010 | Xu et al. |
| 2010/0202969 A1 | 8/2010 | Panyam et al. |
| 2010/0285001 A1 | 11/2010 | Land et al. |

(Continued)

FOREIGN PATENT DOCUMENTS

| EP | 0656422 | 6/1995 |
| EP | 0941998 | 9/2004 |

(Continued)

OTHER PUBLICATIONS

Cheng, G. et al "Mitochondria-targeted drugs synergize with 2-deoxyglucose . . . " Cancer Res., vol. 72, No. 10, pp. 2634-2644. (Year: 2012).*
Yun, J. et al "Vitamin C selectively kills KRAS and BRAF mutant . . . " Science, vol. 350, issue 6266, pp. 1391-1396. (Year: 2015).*
Zielonka et al., "Mitochondria-Targeted Triphenylphosphonium-Based Compounds: Syntheses, Mechanisms of Action, and Therapeutic and Diagnostic Applications", Americal Chemical Society, Chem. Rev. 2017, 117, pp. 10043-10120.
International Search Report for PCT/US2018/028587, mailed.
Written Opinion of the ISA for PCT/US2018/028587, mailed.
Maria Peiris-Pagés et al., "Cancer stem cell metabolism", Breast Cancer Research, Published online May 24, 2016, 18:55, 19 pages.

(Continued)

*Primary Examiner* — Leigh C Maier
(74) *Attorney, Agent, or Firm* — Nixon & Vanderhye, P.C.

(57) ABSTRACT

The present disclosure relates to compounds and methods of eradicating cancer stem cells by combining inhibitors of oxidative metabolism and glycolytic metabolism. Also described are compounds and methods of identifying a combination of inhibitors of oxidative metabolism and glycolytic metabolism to treat cancer stem cells.

6 Claims, 22 Drawing Sheets

(56) References Cited

U.S. PATENT DOCUMENTS

| | | |
|---|---|---|
| 2012/0141467 A1 | 6/2012 | Schneider |
| 2014/0142056 A1 | 5/2014 | Shanmugam et al. |
| 2014/0187611 A1 | 7/2014 | Auwerx et al. |
| 2014/0221301 A1 | 8/2014 | Schimmer et al. |
| 2014/0303085 A1 | 10/2014 | Wong et al. |
| 2014/0364595 A1 | 12/2014 | Bapat et al. |
| 2015/0079154 A1 | 3/2015 | Zender et al. |
| 2015/0125469 A1 | 5/2015 | Liu et al. |
| 2015/0224169 A1 | 8/2015 | Bhatia et al. |
| 2015/0224206 A1 | 8/2015 | Van |
| 2015/0231069 A1 | 8/2015 | Modi |
| 2015/0297723 A1 | 10/2015 | Kisak et al. |
| 2016/0008332 A1 | 1/2016 | Haq et al. |
| 2016/0075726 A1 | 3/2016 | Neuzil |
| 2016/0339106 A1 | 11/2016 | Shanta |
| 2017/0014361 A1 | 1/2017 | Dhar |
| 2017/0035832 A1 | 2/2017 | Liu et al. |
| 2017/0095460 A1 | 4/2017 | Fathi et al. |
| 2017/0224730 A1 | 8/2017 | Berenson |
| 2017/0232008 A1 | 8/2017 | Zeicher |
| 2018/0214472 A1 | 8/2018 | Bapat et al. |

FOREIGN PATENT DOCUMENTS

| | | | |
|---|---|---|---|
| JP | 2016-155679 | 9/2016 | |
| WO | 1995015770 | 6/1995 | |
| WO | 99/26582 | 6/1999 | |
| WO | WO 2008/145116 | 12/2008 | |
| WO | 2010/121177 | 10/2010 | |
| WO | WO 2011/031474 A2 | 3/2011 | |
| WO | 2013/040206 | 3/2013 | |
| WO | WO-2013078554 A1 * | 6/2013 | ............. A61P 35/00 |
| WO | 2015/191668 | 12/2015 | |
| WO | 2016/027089 | 2/2016 | |
| WO | 2016/059247 | 4/2016 | |
| WO | 2018/027252 | 2/2018 | |
| WO | 2018/136598 | 7/2018 | |
| WO | 2018/136617 | 7/2018 | |
| WO | 2018/195434 | 10/2018 | |
| WO | 2018/195446 | 10/2018 | |
| WO | 2018/202910 | 11/2018 | |
| WO | 2018/213751 | 11/2018 | |
| WO | 2018/213764 | 11/2018 | |
| WO | 2018/218242 | 11/2018 | |
| WO | WO 2019104115 | 5/2019 | |
| WO | WO 2019126179 | 6/2019 | |

OTHER PUBLICATIONS

Ernestina Marianna De Francesco et al., "Vitamin C and Doxycycline: A synthetic lethal combination therapy targeting metabolic flexibility in cancer stem cells (CSCs)", ONCOTARGET, Open Access Impact Journal, Published online Jun. 9, 2017, 27 pages.

U.S. Appl. No. 10/188,668, filed Jan. 29, 2019, Bannister et al.

Lamb, et al., "Antibiotics that target mitochondria effectively eradicate cancer stem cells, across multiple tumor types: Treating cancer like an infectious disease", Oncotarget, Jan. 22, 2015, vol. 6, No. 7, pp. 4569-4584.

Giacometti et al., "In-vitro activity of macrolides alone and in combination with artemisin, atovaquone, dapsone, minocycline or pyrimethamine against *Cryptosporidium parvum*", Journal of Antimicrobial Chemotherapy, 1996, vol. 38, pp. 399-408.

M2 Pharma [London], "Study finds vitamin C and antibiotics effectively killed cancer stem cells", Jun. 13, 2017, 2 pages.

Sotgia et al., "A mitochondrial based oncology platform for targeting cancer stem cells (CSCs): MITO-ONC-RX", Journal Cell Cycle, Sep. 26, 2018, vol. 17, No. 17, pp. 2091-2100.

Komatsu et al., "Clarithromycin enhances bortezomib-induced cytotoxicity via endoplasmic reticulum stress-mediated CHOP (GADD153) induction and autophagy in breast cancer cells", International Journal of Oncology, vol. 40, 2012, pp. 1029-1039.

Moriya et al., "Macrolide antibiotics block autophagy flux and sensitize to bortezomib via endoplasmic reticulum stress-mediated CHOP induction in myeloma cells", International Journal of Oncology, vol. 42, 2013, pp. 1541-1550.

Petovari et al., "Targeting cellular metabolism using rapamycin and/or doxycycline enhances anti-tumour effects in human glioma cells", Cancer Cell Int., 18:211, 2018, pp. 1-17.

Van Nuffel et al., "Repurposing Drugs in Oncology (ReDO)—clarithromycin as an anti-cancer agent", ecancermedicalscience, 2015, pp. 1-26.

Jankowitsch et al., "A novel N,N-8-amino-8-demethyl-D-riboflavin dimethyltransferase (RosA) catalyzing the two terminal steps of roseoflavin biosynthesis in *Streptomyces davawensis*", The American Society for Biochemistry and Molecular Biology, Inc., 2011, pp. 1-25.

Murphy, "Targeting lipophilic cations to mitochondria", Biochimica et Biophysica Acta, 2008, pp. 1028-1031.

Ross et al., "Lipophilic Triphenylphosphonium Cations as Tools in Mitochondrial Bioenergetics and Free Radical Biology", Biochemistry (Moscow), vol. 70, No. 2, 2005, pp. 222-230. [Translated from Biokhimiya].

Gonzalez et al., "Mitochondria, Energy and Cancer: The Relationship with Ascorbic Acid", JOM, vol. 25, No. 1, 2010, pp. 29-38.

* cited by examiner

VITAMIN C AND DOXYCYCLINE: A SYNTHETIC LETHAL COMBINATION THERAPY FOR ERADICATING CANCER STEM CELLS (CSCS)

CROSS-REFERENCE TO RELATED APPLICATIONS

This application is the U.S. national phase of International Application No. PCT/US2018/028587 filed Apr. 20, 2018, which designated the U.S. and claims the benefit of U.S. Provisional Patent Application No. 62/488,489, filed Apr. 21, 2017, the entire contents of each of which are hereby incorporated herein by reference.

FIELD

The present disclosure relates to methods of eradicating cancer stem cells by combining inhibitors of oxidative metabolism and glycolytic metabolism.

BACKGROUND

Researchers have struggled to develop new anti-cancer treatments. Conventional cancer therapies (e.g. irradiation, alkylating agents such as cyclophosphamide, and anti-metabolites such as 5-Fluorouracil) have attempted to selectively detect and eradicate fast-growing cancer cells by interfering with cellular mechanisms involved in cell growth and DNA replication. Other cancer therapies have used immunotherapies that selectively bind mutant tumor antigens on fast-growing cancer cells (e.g., monoclonal antibodies). Unfortunately, tumors often recur following these therapies at the same or different site(s), indicating that not all cancer cells have been eradicated. Relapse may be due to insufficient chemotherapeutic dosage and/or emergence of cancer clones resistant to therapy. Hence, novel cancer treatment strategies are needed.

Advances in mutational analysis have allowed in-depth study of the genetic mutations that occur during cancer development. Despite having knowledge of the genomic landscape, modern oncology has had difficulty with identifying primary driver mutations across cancer subtypes. The harsh reality appears to be that each patient's tumor is unique, and a single tumor may contain multiple divergent clone cells. What is needed, then, is a new approach that emphasizes commonalities between different cancer types. Targeting the metabolic differences between tumor and normal cells holds promise as a novel cancer treatment strategy. An analysis of transcriptional profiling data from human breast cancer samples revealed more than 95 elevated mRNA transcripts associated with mitochondrial biogenesis and/or mitochondrial translation. Sotgia et al., *Cell Cycle,* 11(23):4390-4401 (2012). Additionally, more than 35 of the 95 upregulated mRNAs encode mitochondrial ribosomal proteins (MRPs). Proteomic analysis of human breast cancer stem cells likewise revealed the significant overexpression of several mitoribosomal proteins as well as other proteins associated with mitochondrial biogenesis. Lamb et al., *Oncotarget,* 5(22):11029-11037 (2014). Functional inhibition of mitochondrial biogenesis using the off-target effects of certain bacteriostatic antibiotics or OXPHOS inhibitors provides additional evidence that functional mitochondria are required for the propagation of cancer stem cells.

There exists a need in the art for novel anticancer strategies, new compounds with broad-spectrum antibiotic activity, and compounds to reduce the effects of aging. The "endosymbiotic theory of mitochondrial evolution" can be used as the basis for the development of therapies to treat drug-resistance that is characteristic of both tumor recurrence and infectious disease, and such therapies may have the additional benefit of slowing the aging process.

In view of the foregoing, it is therefore an objective of this disclosure to demonstrate that mitochondrial biogenesis plays a critical role in the propagation and maintenance of many cancers. It is also an objective of this disclosure to demonstrate that the combination of mitochondrial-targeting compounds and glycolysis-targeting compounds may be used to eradicate cancer stem cells (CSCs) by metabolically "starving" the CSCs. It is also an objective of this disclosure to present methods for identifying and using the combination of mitochondrial-targeting compounds and glycolysis-targeting compounds for therapeutic purposes.

The inventors analyzed phenotypic properties of CSCs that could be targeted across a wide range of cancer types and identified a strict dependence of CSCs on mitochondrial biogenesis for the clonal expansion and survival of CSCs. Previous work by the inventors demonstrated that different classes of FDA-approved antibiotics, and in particular tetracyclines, such as doxycycline, and erythromycin have an off-target effect of inhibiting mitochondrial biogenesis. Such compounds could have efficacy for eradicating CSCs. Unfortunately, when used alone these antibiotics do not eradicate all CSCs; rather, these antibiotics metabolically synchronize a surviving CSC sub-population from oxidative metabolism to glycolytic metabolism, resulting in metabolic inflexibility. The present disclosure demonstrates that the use of compounds that metabolically target the antibiotic-resistant CSC sub-population in combination with the mitochondrial-targeting compounds may be used to eradicate CSCs.

SUMMARY

The present disclosure relates to methods of treating cancer by administering to a patient in need thereof of a pharmaceutically effective amount of an inhibitor of oxidative metabolism and an inhibitor of glycolytic metabolism. Inhibitors of oxidative metabolism may include members of tetracycline family and the erythromycin family. Members of the tetracycline family include tetracycline, doxycycline, tigecycline, minocycline, chlortetracycline, oxytetracycline, demeclocycline, lymecycline, meclocycline, methacycline, rolitetracycline, chlortetracycline, omadacycline, and sarecycline. Members of the erythromycin family include erythromycin, azithromycin, and clarithromycin. Inhibitors of glycolytic may be selected from inhibitors of glycolysis, inhibitors of OXPHOS, and inhibitors of autophagy. Inhibitors of glycolysis include 2-deoxy-glucose, ascorbic acid, and stiripentol. Inhibitors of OXPHOS include atorvaquone, irinotecan, sorafenib, niclosamide, and berberine chloride. Inhibitors of autophagy include chloroquine.

The present disclosure also relates to methods of identifying a combination of inhibitors of oxidative metabolism and glycolytic metabolism to treat cancer stem cells, the method comprising: chronically treating cancer stem cells with at least one inhibitor of oxidative metabolism; confirming the chronically treated cancer stem cells manifest a glycolytic phenotype; further treating the chronically treated cancer stem cells with at least one inhibitor of glycolytic metabolism; and confirming inhibition of glycolytic metabolism. These methods may include treating MCF7 cells. The at least one inhibitor of oxidative metabolism may be selected from the tetracycline family and/or at least one member of the erythromycin family. The member of the tetracycline family may be selected from the group comprising at least one of tetracycline, doxycycline, tigecycline, minocycline, chlortetracycline, oxytetracycline, demeclocycline, lymecycline, meclocycline, methacycline, rolitetracycline, chlortetracycline, omadacycline, and sarecycline. The member of the erythromycin family may be selected from the group comprising at least one of erythromycin, azithromycin, and clarithromycin. Confirming that the chronically treated cancer stem cells manifest a glycolytic phenotype may include performing metabolic flux analysis and/or performing label-free unbiased proteomics. Metabolic flux analysis may include measuring oxygen consumption rates, measuring extracellular acidification rates, and measuring mammosphere formation. Performing label-free unbiased proteomics may include measuring relative changes to mitochondrial protein levels and/or measuring relative changes to glycolytic enzyme levels. The at least one inhibitor of glycolytic metabolism may be selected from the group comprising an inhibitor of glycolysis, an inhibitor of OXPHOS, and an inhibitor of autophagy. Inhibitors of glycolysis include 2-deoxy-glucose, ascorbic acid, and stiripentol. Inhibitors of OXPHOS include atoravaquone, irinotecan, sorafenib, niclosamide, and berberine chloride. Inhibitors of autophagy include chloroquine. Confirming inhibition of glycolytic metabolism may include measuring mammosphere formation.

BRIEF DESCRIPTION OF THE DRAWINGS

FIGS. 1A-C show the effects of increasing concentrations of doxycycline over time on mitochondrial mass (1A shows effects of 12.5 µM doxycycline treatment, 1B shows effects of 25 µM doxycycline treatment, 1C shows effects of 50 µM doxycycline treatment). FIG. 1D shows representative plots illustrating increased mitochondrial mass of doxycycline-resistant MCF7 cells as compared to untreated MCF7 cells. FIG. 1E shows confirmation of mitochondrial mass by immuno-blot analysis with specific antibodies directed against TOMM20, an established marker of mitochondrial mass.

DESCRIPTION

The following description illustrates embodiments of the present approach in sufficient detail to enable practice of the present approach. Although the present approach is described with reference to these specific embodiments, it should be appreciated that the present approach can be embodied in different forms, and this description should not be construed as limiting any appended claims to the specific embodiments set forth herein. Rather, these embodiments are provided so that this disclosure will be thorough and complete, and will fully convey the scope of the present approach to those skilled in the art.

The mitochondrial ribosome is an untapped gateway for treating a number of afflictions, ranging from cancer to bacterial and fungal infections to aging. Functional mitochondria are required for the propagation of CSCs. Inhibiting mitochondrial biogenesis in cancer cells impedes the propagation of those cells. Mitochondrial inhibitors therefore represent a new class of anti-cancer therapeutics. In some cases, however, a surviving cancer cell sub-population may metabolically synchronize toward a glycolytic phenotype. The inventors hypothesized that combining an inhibitor of glycolysis with a mitochondrial inhibitor may present a method for eradicating CSCs.

To test this hypothesis, the inventors generated a cancer cell sub-population metabolically synchronized toward a glycolytic phenotype by chronically treating MCF7 cells with the FDA-approved antibiotic doxycycline, a mitochondrial inhibitor. Briefly, MCF7 cells were obtained from ATCC and cultured in DMEM (Sigma Aldrich). MCF7 cells resistant to doxycycline (MCF7-DoxyR cells) were selected by a stepwise exposure to increasing concentrations of doxycycline. Specifically, MCF7 cells were initially exposed to 12.5 µM doxycycline, followed by 3 weeks of treatment with 25 µM doxycycline, followed by 3 weeks of treatment with 50 µM doxycycline. The doxycycline-resistant MCF7 cells were then routinely maintained in regular medium supplemented with 25 µM Doxycycline. It should be appreciated that other cancer cell lines and other mitochondrial (oxidation) inhibitors may be used.

Figure 1A:
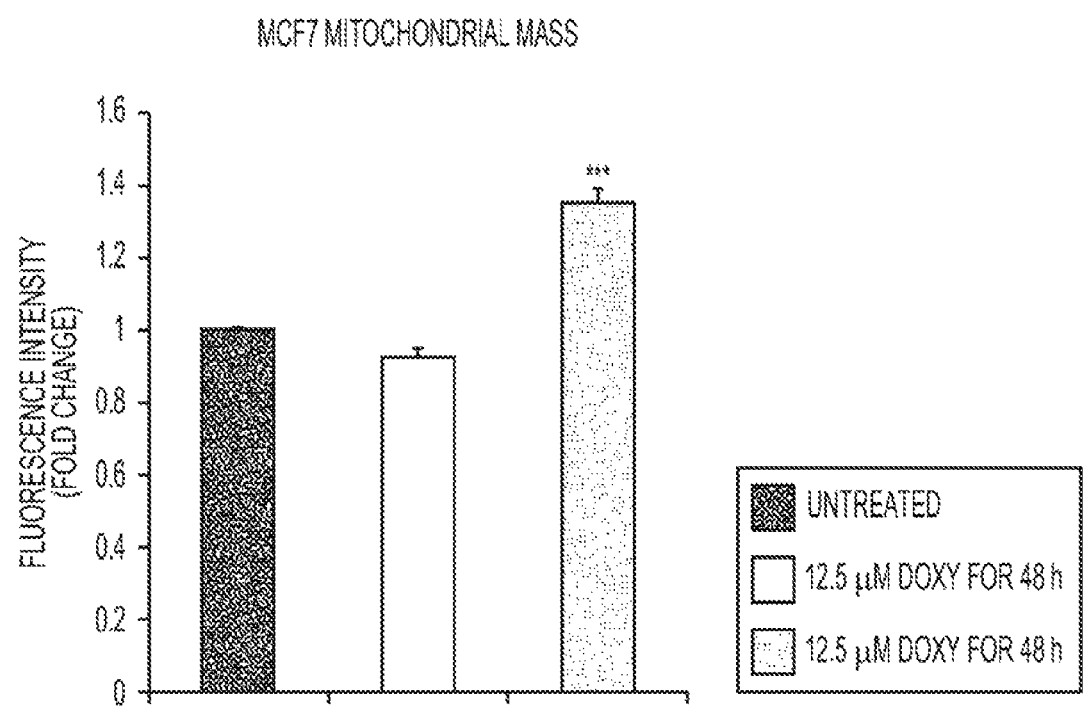
FIGS. 1A-E show the effects of doxycycline treatment on mitochondrial mass.
Figure 1B:
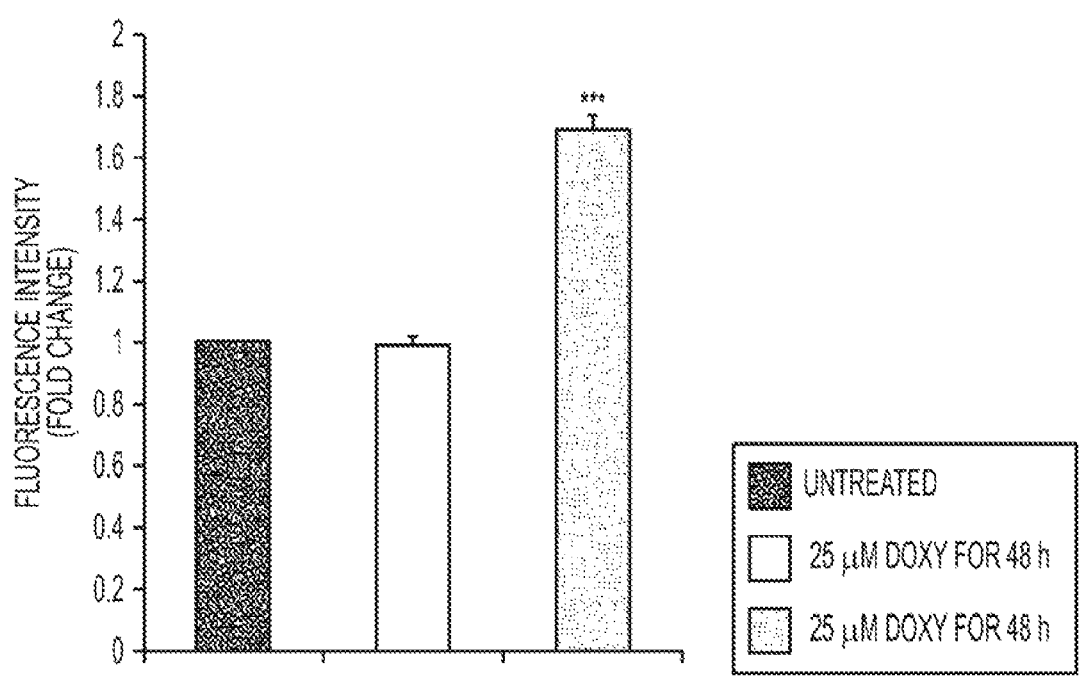
Figure 1C:
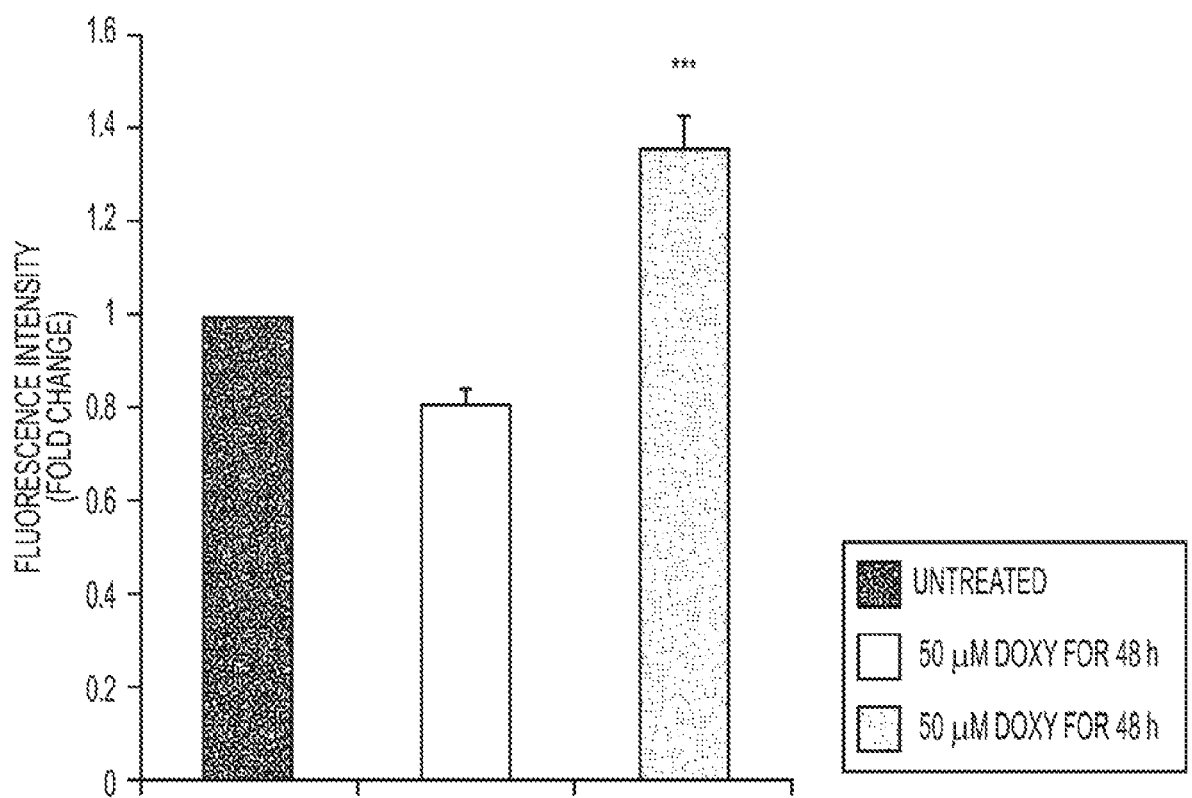
Figure 1D:
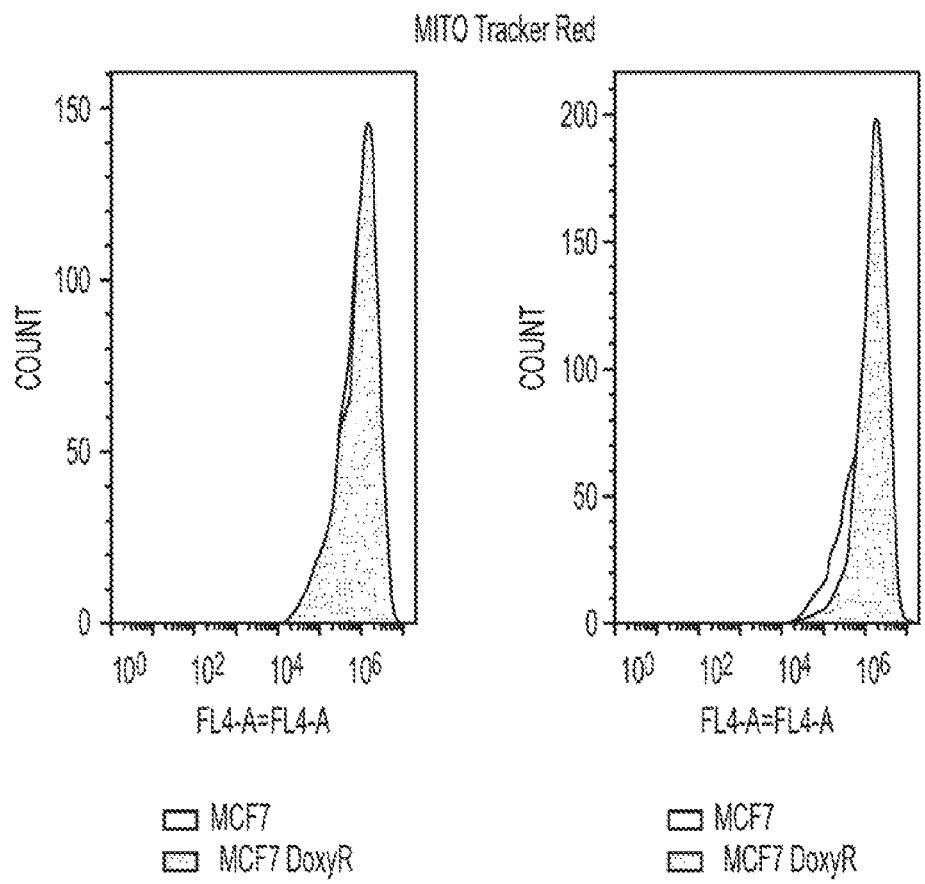
Figures 1E, 1F:
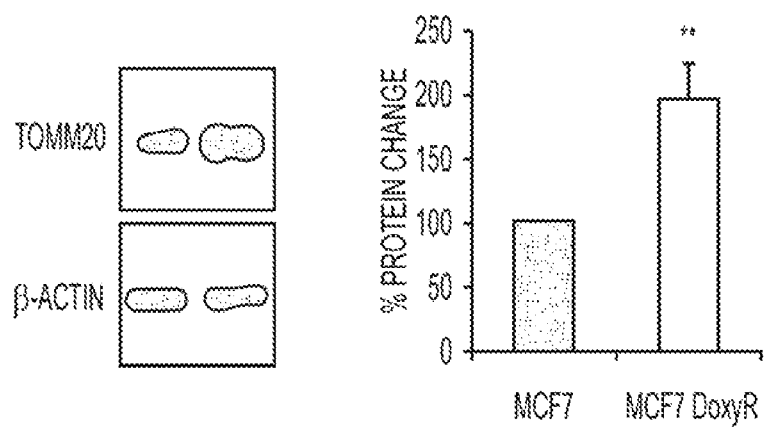
Figure 2A:
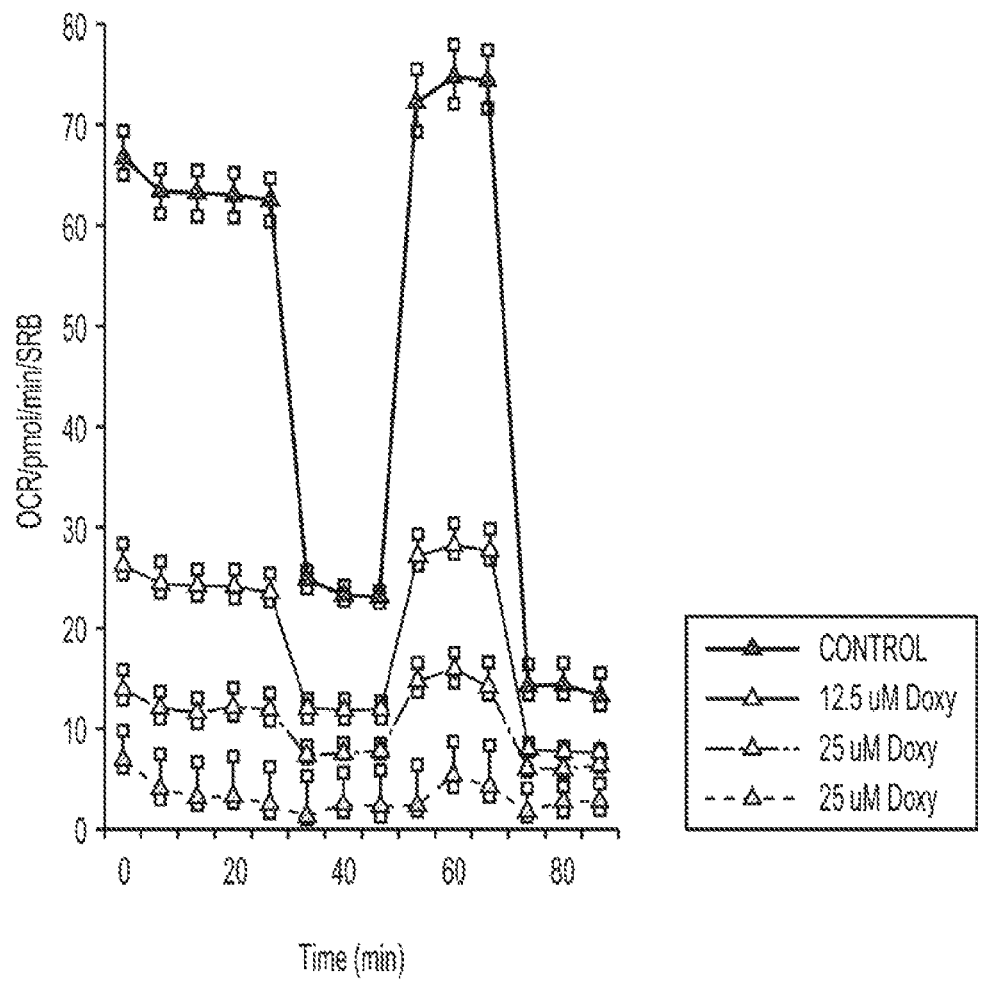
FIG. 2A illustrates the effects of doxycycline treatment on oxygen consumption rate (OCR) over time in MCF7 cells.
Figure 2B:
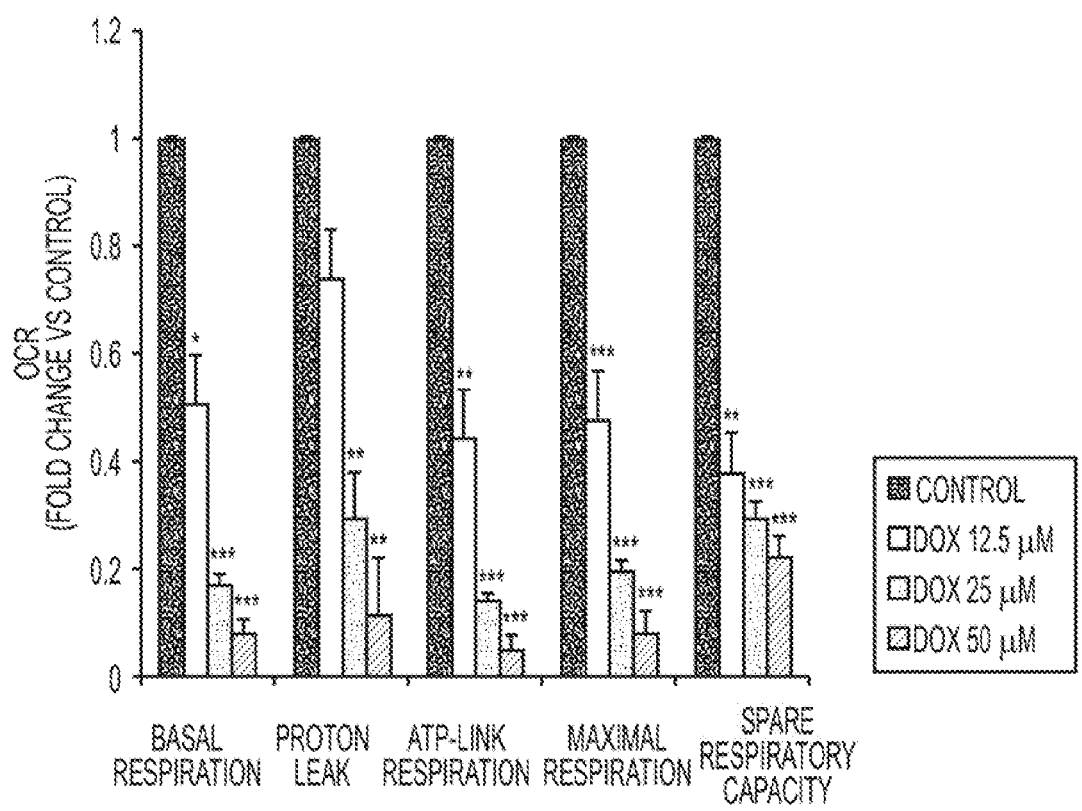
FIG. 2B shows the effects of doxycycline treatment on OCR for basal respiration, proton leak, ATP-linked respiration, maximal respiration, and spare respiratory capacity.

The present approach further involves methods of analyzing the effects of chronic treatment on cells by considering changes to mitochondrial mass. The inventors measured mitochondrial mass by FACS analysis, but it should be appreciated that other methods known in the art to measure mitochondrial mass may be used. Briefly, cells were stained with MitoTracker Deep Red (Life Technologies), which localizes to mitochondria regardless of mitochondrial membrane potential. Cells were incubated with pre-warmed MitoTracker staining solution (diluted in PBS/CM to a final concentration of 10 nM) for 30-60 min at 37° C. All subsequent steps were performed in the dark. Cells were washed in PBS, harvested, re-suspended in 300 µL of PBS and then analyzed by flow cytometry (Fortessa, BD Bioscience, Calif., USA). Data analysis was performed using FlowJo software. Extracellular acidification rates (ECAR) and real-time oxygen consumption rates (OCR) for MCF7 cells were determined using the Seahorse Extracellular Flux (XFe-96) analyzer (Seahorse Bioscience, Mass., USA). 15,000 MCF7 and MCF7 DoxyR cells per well were seeded into XFe-96 well cell culture plates for 24 h. Then, cells were washed in pre-warmed XF assay media (or for OCR measurement, XF assay media supplemented with 10 mM glucose, 1 mM Pyruvate, 2 mM L-glutamine and adjusted at 7.4 pH). Cells were then maintained in 175 µL/well of XF assay media at 37 C, in a non-$CO_2$ incubator for 1 hour. During the incubation time, 5 µL of 80 mM glucose, 9 µM oligomycin, and 1 M 2-deoxyglucose (for ECAR measurement) or 10 µM oligomycin, 9 µM FCCP, 10 µM Rotenone, 10 µM antimycin A (for OCR measurement), were loaded in XF assay media into the injection ports in the XFe-96 sensor cartridge. Data set was analyzed by XFe-96 software after the measurements were normalized by protein content (SRB). All experiments were performed three times independently. FIGS. 2A-D show that MCF7-DoxyR cells exhibit a significant increase in mitochondrial mass (by ~1.3- to 1.7-fold), as compared to acute treatment with doxycycline at the same drug concentration. The overall increase in mitochondrial mass was confirmed by immunoblot analysis with specific antibodies directed against TOMM20, a well-established marker of mitochondrial mass (FIG. 1E).

Figure 3:
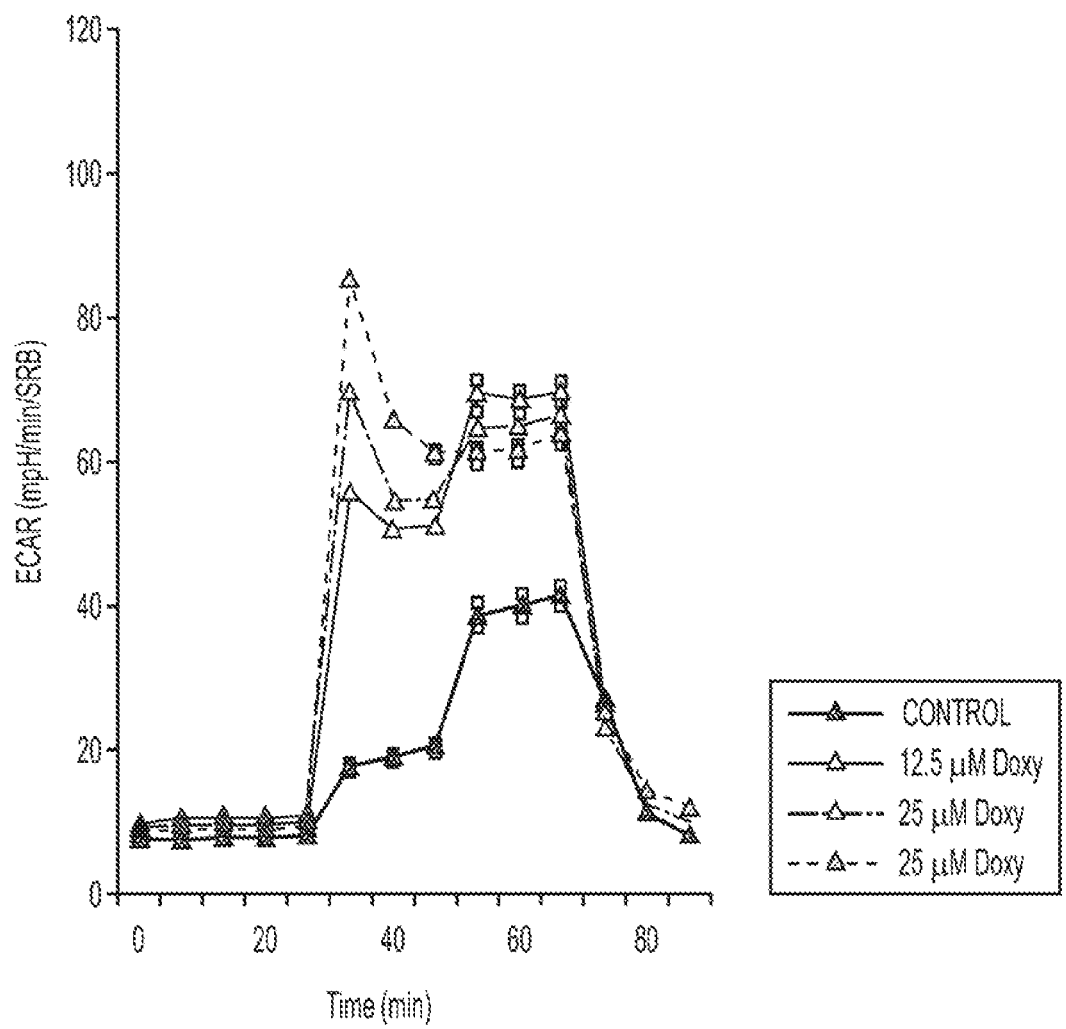
FIG. 3 shows the effects of doxycycline treatment on extracellular acidification rate (ECAR) over time in MCF7 cells.
Figure 4:
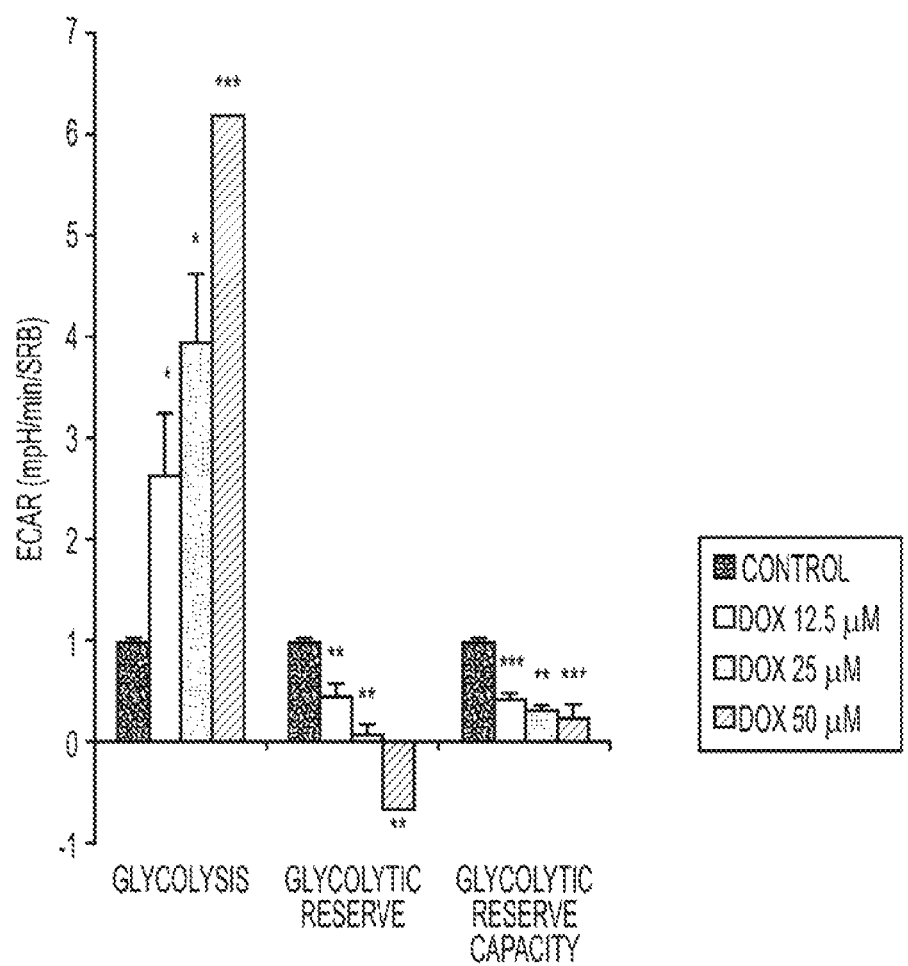
FIG. 4 shows the effects of doxycycline treatment on ECAR for glycolysis, glycolytic reserve, and glycolytic reserve capacity.
Figure 5A:
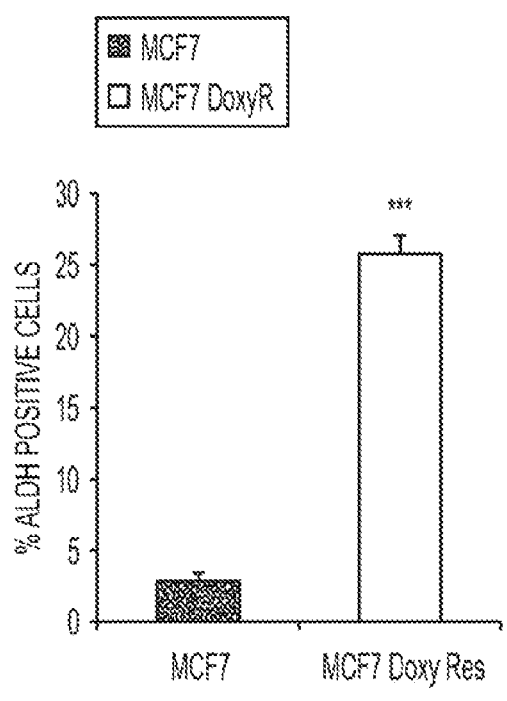
FIGS. 5A and 5C show the effects of doxycycline treatment on CSC markers ALDH and $CD44^+/CD24^{low}$ activity, respectively.
Figure 5B:
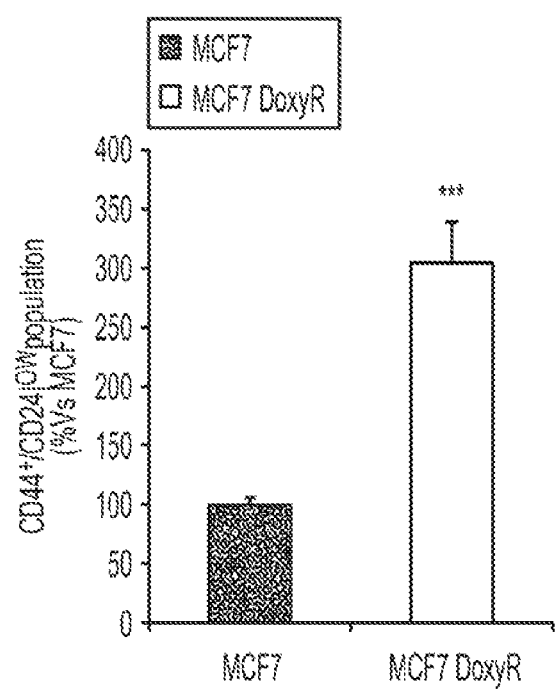
FIGS. 5B and 5D-E shows the effects of doxycycline treatment on CD24 and CD44 using fluorescence activated cell sorting (FACS).
Figure 5C:
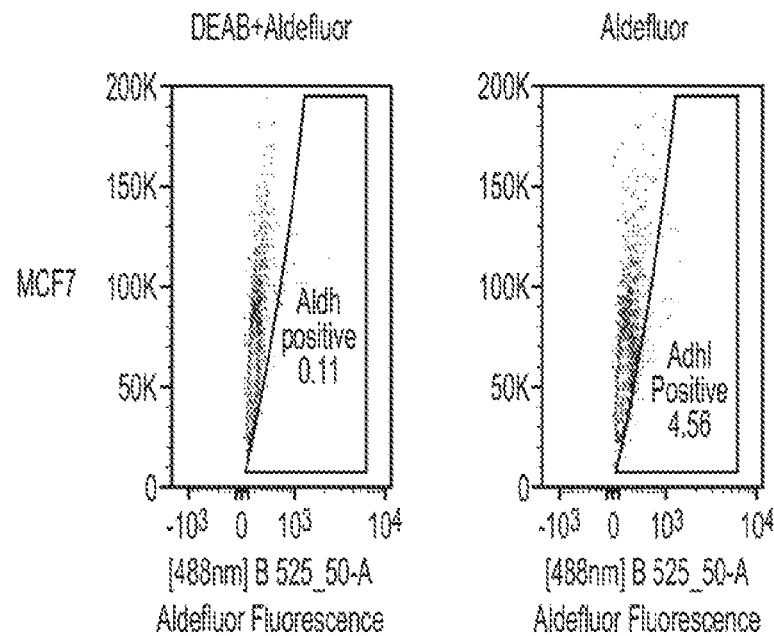
Figure 5E:
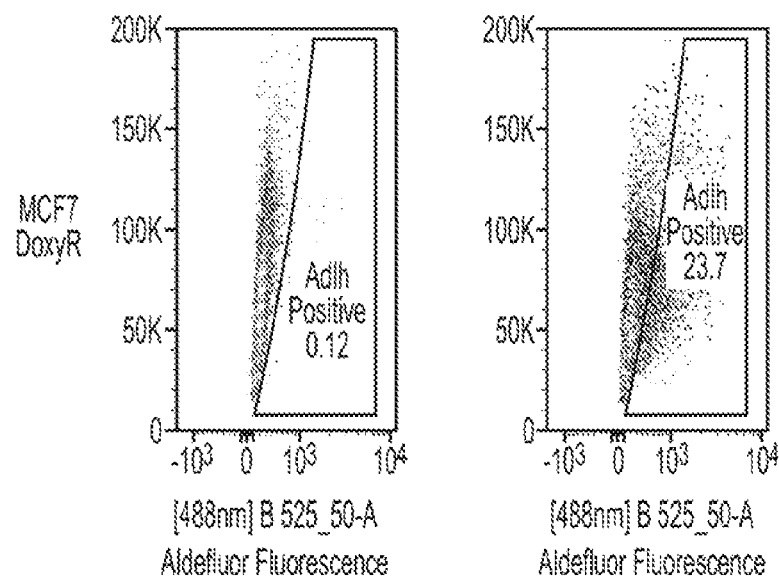
Figure 5D:
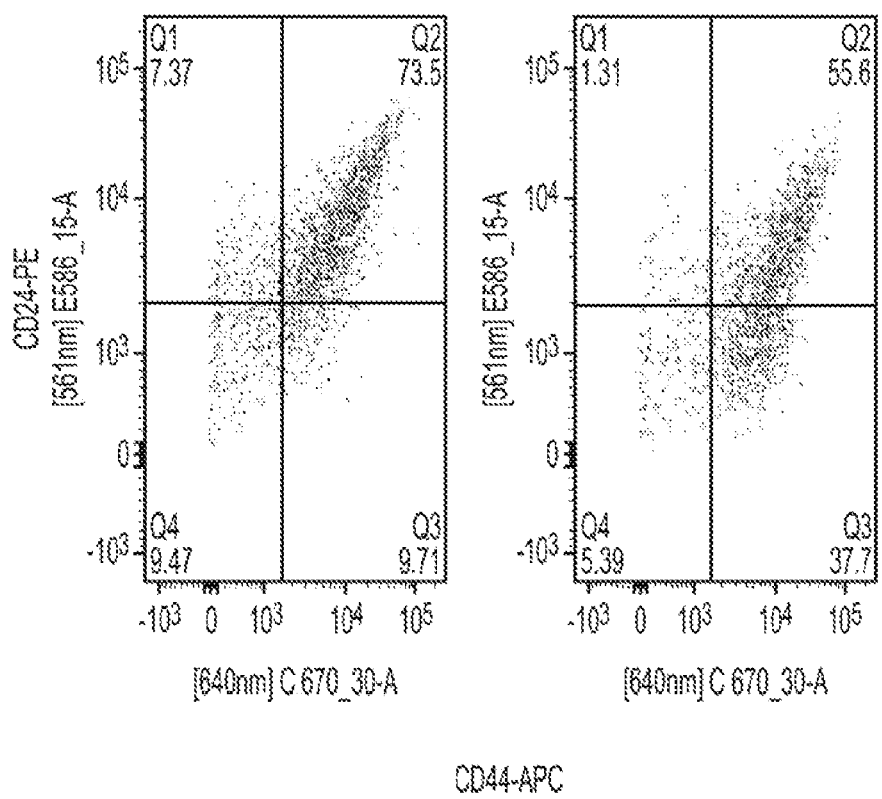

The present approach also includes methods of analyzing the effects of chronic treatment on cells by considering changes to oxygen consumption rates. FIGS. 3A-B show that MCF7-DoxyR cells also exhibited a significant reduction in oxygen consumption rates (OCR), as compared to control MCF7 cells. Reduced OCR suggests that ATP levels are severely depleted in the MCF7-DoxyR cells. Conversely, glycolysis was substantially increased in the MCF7-DoxyR cells as measured by the ECAR (extracellular acidification rate) (FIGS. 3 and 4). Therefore, the generated DoxyR cells were mainly glycolytic, thus validating the hypothesis that a sub-population of CSCs may survive and develop doxycycline-resistance by adopting a purely glycolytic phenotype.

The present approach further involves methods of analyzing the effects of chronic treatment on cells by examining relative changes of CSC markers and functional CSC activity using, for example, mammosphere, proliferation, and cell migration assays. For example, aldehyde dehydrogenase (ALDH) activity and CD44/CD24 levels are routinely used as markers to identify breast CSCs. ALDH activity may be assessed by FACS analysis. The ALDEFLUOR kit (StemCell Technologies, Mass., USA) may be used to isolate the population with high ALDH enzymatic activity. Briefly, $1 \times 10^5$ MCF7 and MCF7 DoxyR cells may be incubated in 1 ml ALDEFLUOR assay buffer containing ALDH substrate (5 µl/ml) for 40 minutes at 37° C. In each experiment, a sample of cells may be stained under identical conditions with 30 µM of diethylaminobenzaldehyde (DEAB), a specific ALDH inhibitor, as a negative control. The ALDEFLUOR-positive population may be established according to the manufacturer's instructions and evaluated in $3 \times 10^4$ cells. Data analysis may be performed using FlowJo software. An Anoikis assay may be used to determine CD24/CD44 expression. Briefly, MCF7 and MCF7 DoxyR cells may be seeded on low-attachment plates to enrich for the CSC population. Under these conditions, the non-CSC population undergoes anoikis (a form of apoptosis induced by a lack of cell-substrate attachment) and CSCs are believed to survive. The surviving CSC fraction may be analyzed by FACS analysis. Briefly, $1 \times 10^5$ MCF7 and MCF7 DoxyR monolayer cells may be seeded for 48 h in 6-well plates. Then, cells may be trypsinized and seeded in low-attachment plates in mammosphere media. After 10 h, cells may be spun down and incubated with CD24 (IOTest CD24-PE, Beckman Coulter) and CD44 (APC mouse Anti-Human CD44, BD Pharmingen) antibodies for 15 minutes on ice. Cells may be rinsed twice and incubated with LIVE/DEAD dye (Fixable Dead Violet reactive dye; Life Technologies) for 10 minutes. Samples may then be analyzed by FACS. Only the live population, as identified by the LIVE/DEAD dye staining, may be analyzed for CD24/CD44 expression using FlowJo software. FIGS. 5A-D show MCF7-DoxyR cells have a substantial increase in ALDH activity and CD44/CD24 levels. Notably, ALDH activity and CD44/CD24 levels do not reflect active CSC activity.

Figure 6A:
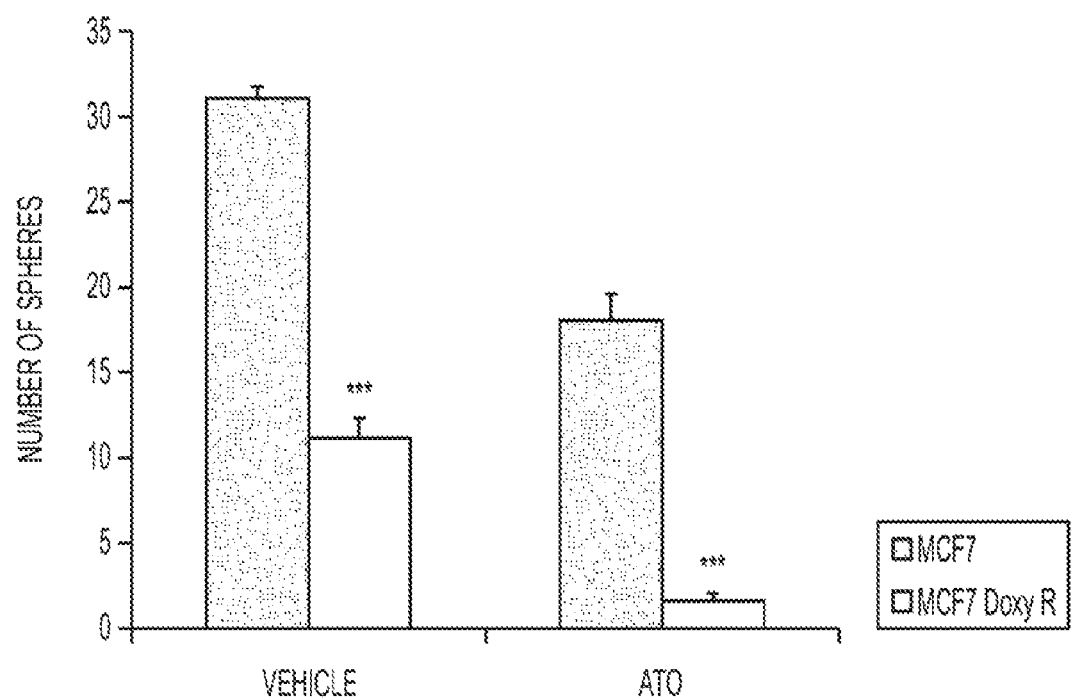
FIGS. 6A-B show the effects of Atovaquone and Cloroquine on the propagation of doxycycline-treated and untreated MCF7 cells.
Figure 6B:
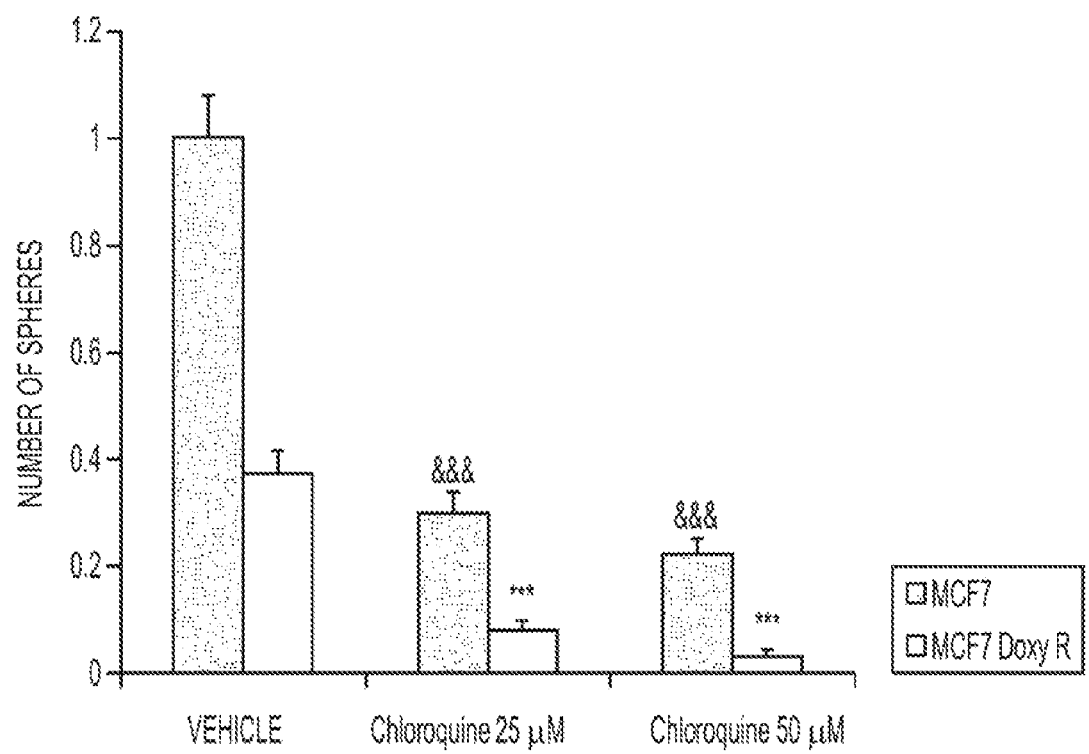

To more directly assess functional CSC activity, mammosphere formation assays may be used. Briefly, a single cell suspension of MCF7 or MCF7 DoxyR cells may be prepared using enzymatic (1× Trypsin-EDTA, Sigma Aldrich), and manual disaggregation (25-gauge needle). Cells may be plated at a density of 500 cells/cm2 in mammosphere medium (DMEM-F12/B27/20-ng/ml EGF/PenStrep) in nonadherent conditions, in culture dishes coated with (2-hydroxyethylmethacrylate) (poly-HEMA, Sigma), in the presence of Atovaquone (FIG. 6A) or Chloroquine (FIG. 6B). Cells may be grown for 5 days and maintained in a humidified incubator at 37° C. at an atmospheric pressure in 5% (v/v) carbon dioxide/air. After 5 days for culture, spheres larger than 50 µm may be counted using an eye piece graticule, and the percentage of cells plated which formed spheres may be calculated. Mammosphere assays may be performed in triplicate and repeated three times independently. FIG. 6 shows that MCF7-DoxyR cell propagation is significantly more sensitive to Atovaquone, as compared with control MCF7 CSCs. Specifically, treatment with 1 µM Atovaquone inhibited the CSC propagation of MCF7-DoxyR cells by more than 85%. Similarly, Chloroquine inhibited propagation by more than 75% at 25 µM and by more than 90% at 50 µM. These results suggest it is possible to target the propagation of DoxyR CSCs using existing FDA-approved OXPHOS and autophagy inhibitors. Therefore, increases in CSC marker levels do not necessarily reflect functional increases in CSC propagation.

To determine functional effects on doxycycline on CSC propagation, proliferation may be measured by determining relative levels of EdU incorporation (EdU refers to the alkyne-containing thymidine analog (5-ethynyl-2'-deoxyuridine) which is incorporated into DNA during active DNA synthesis). For example, 48 h after seeding MCF7 and MCF7-DoxyR cells were subjected to a proliferation assay using Click-iT Plus EdU Pacific Blue Flow Cytometry Assay Kit (Life Technologies) customized for flow cytometry. Briefly, cells were treated with 10 µM EdU for 2 hours and then fixed and permeabilized. EdU was detected after permeabilization by staining cells with Click-iT Plus reaction cocktail containing the Fluorescent dye picolylazide for 30 min at room temperature. Samples were then washed and analyzed using flow cytometer. Background values were estimated by measuring non-EdU labeled, but Click-iT stained cells. Data were analyzed using FlowJo software.

Figure 7A:
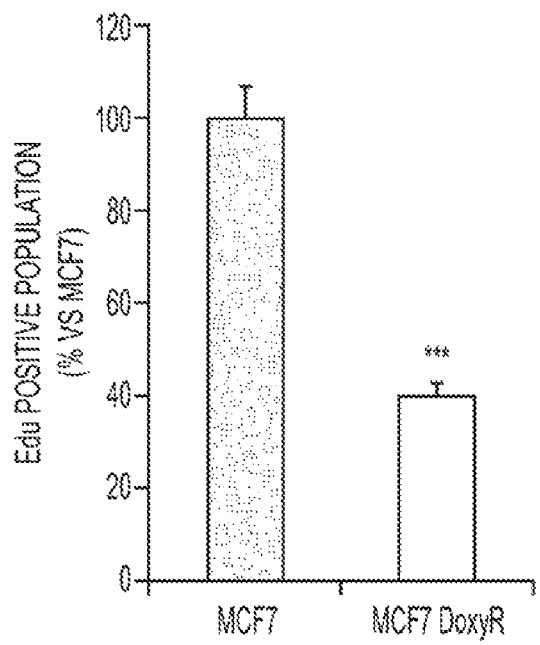
FIG. 7A shows the effects of doxycycline treatment on cell proliferation using an EdU incorporation assay.
Figure 7B:
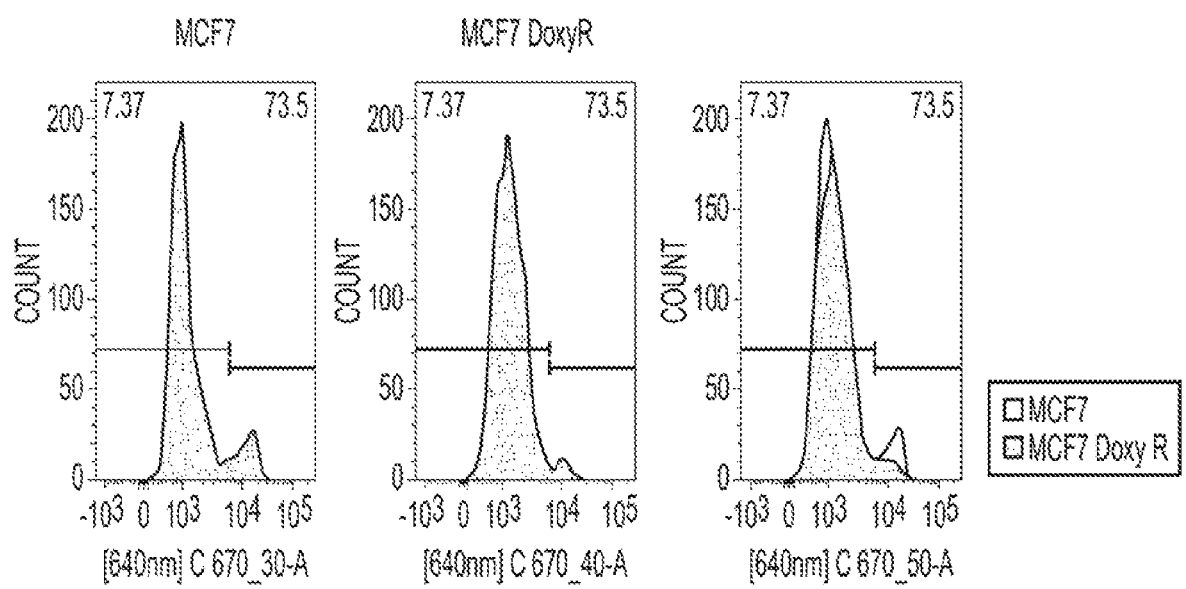
FIG. 7B shows the reduction of the EdU positive population in doxycycline-treated MCF7 cells as compared to MCF7 cells using FACS.

FIGS. 7A-B show MCF7-DoxyR cells have a reduced ability to proliferate by more than 60%, as measured using EdU-incorporation.

Figure 7C:
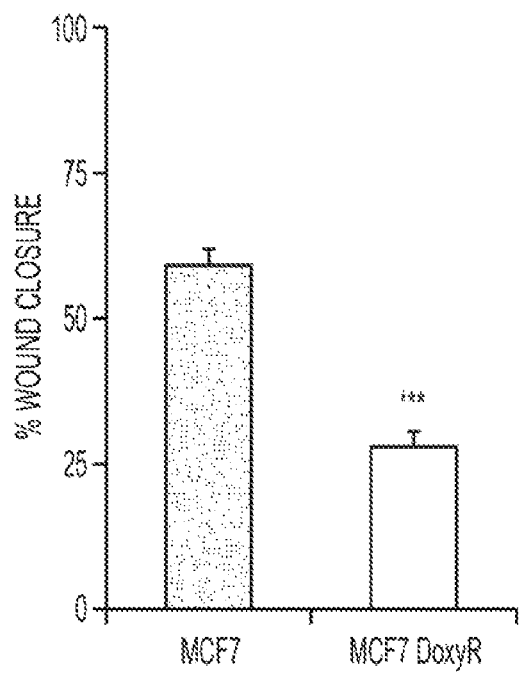
FIG. 7C shows the effects of doxycycline treatment on cell migration using a wound healing assay.
Figure 7D:
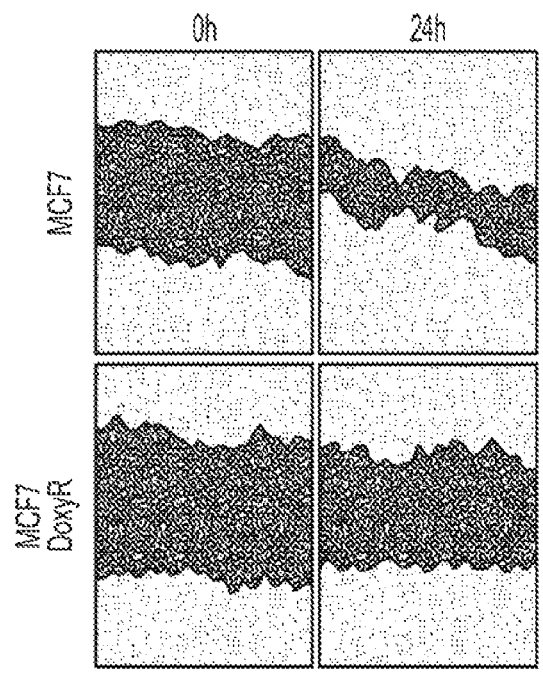
FIG. 7D provides images of cells tested using the scratch assay.

The present approach further involves methods of analyzing the effects of chronic treatment on functionality by considering cell migration. MCF7-DoxyR cells also show a clear defect in cell migration, with a greater than 50% reduction, as observed using the standard "scratch assay" (FIG. 7C-D). To determine cell migration, MCF7 and MCF7 DoxyR cells were allowed to grow in regular growth medium until they were 70-80% confluent. Next, to create a scratch of the cell monolayer, a p200 pipette tip was used. Cells were washed twice with PBS and then incubated at 37° C. in regular medium for 24 h. The migration assay was evaluated using Incucyte Zoom (Essen Bioscience). The rate of migration was measured by quantifying the % of wound closure area, determined using the software ImageJ, according to the formula: % of wound closure=[(At=0 h−At=Δh)/At=0 h]×100%. Data was represented as the mean±standard error of the mean (SEM), taken over ≥3 independent experiments, with ≥3 technical replicates per experiment. Statistical significance was measured using the t-test. $P \leq 0.05$ was considered significant.

Figure 7E:
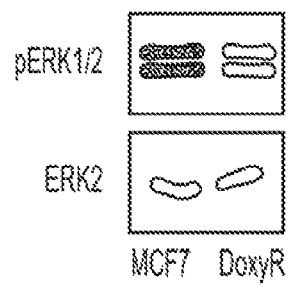
FIG. 7E-F show the effects of doxycycline on ERK1/2 and AKT Ser 473 phosphorylation, respectively.
Figure 7F:
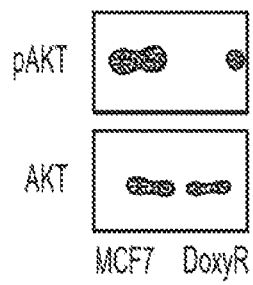

Phosphorylation levels of proteins involved in cell signaling, such as ERK and AKT, may be investigated to further determine cell phenotype. To determine ERK and AKT phosphorylation, MCF7 and MCF7 DoxyR cells protein lysates were electrophoresed through a reducing SDS/10% (w/v) polyacrylamide gel, electroblotted onto a nitrocellulose membrane and probed with primary antibodies against phosphorylated AKT (Ser 473) and ATK (Cell Signaling), phopshorylated ERK 1/2 (E-4), ERK2 (C-14), TOMM20 (F-10) and β-actin (C2) (all purchased from Santa Cruz Biotechnology). Proteins were detected by horseradish peroxidase-linked secondary antibodies and revealed using the SuperSignal west pico chemiluminescent substrate (Fisher Scientific). FIGS. 7E-F show MCF7-DoxyR cells have significant reductions in ERK-activation and AKT-activation. These findings demonstrate that MCF7-DoxyR cells have a quiescent glycolytic cell phenotype.

To further validate the functional observations from metabolic flux analysis, unbiased label-free proteomics analysis may be conducted. Briefly, cell lysates may be prepared for trypsin digestion by sequential reduction of disulphide bonds with TCEP and alkylation with MMTS. Peptides may be extracted and prepared for LC-MS/MS. All LC-MS/MS analyses may be performed on an LTQ Orbitrap XL mass spectrometer (Thermo Scientific, San Jose, Calif.) coupled to an Ultimate 3000 RSLC nano system (Thermo Scientific, formerly Dionex, NL). Xcalibur raw data files acquired on the LTQ-Orbitrap XL may be directly imported into Progenesis LCMS software (Waters Corp., Milford, Mass., USA, formerly Non-Linear Dynamics, Newcastle upon Tyne, UK) for peak detection and alignment. Data may be analyzed using the Mascot search engine. Five technical replicates may be analyzed for each sample type.

TABLE 1

Key Mitochondrial-Related Proteins are Down-Regulated in Doxy-Resistant MCF7 Cells.

| Symbol | Description | Fold-reduction (Down-regulation) |
|---|---|---|
| Mitochondrial proteins encoded by mitochondrial DNA | | |
| MT-ND3 | NADH-ubiquinone oxidoreductase chain 3 (Complex I) | 35.07 |
| MT-CO2 | Cytochrome c oxidase subunit 2 (Complex IV) | 19.26 |
| MT-ATP8 | ATP synthase protein 8 (Complex V) | 6.42 |
| MT-ATP6 | ATP synthase subunit 6 (Complex V) | 5.08 |
| Mitochondrial proteins encoded by nuclear DNA | | |
| NDUFS1 | NADH-ubiquinone oxidoreductase 75 kDa subunit, mitochondrial | 12.53 |
| NNT | NAD(P) transhydrogenase, mitochondrial | 10.49 |
| SSBP1 | Single-stranded DNA-binding protein, mitochondrial | 9.27 |
| NDUFB8 | NADH dehydrogenase 1 beta subcomplex subunit 8, mitochondrial | 8.5 |
| CKMT1A | Creatine kinase U-type, mitochondrial | 7.49 |
| TFAM | Transcription factor A, mitochondrial | 6.89 |
| COX7C | Cytochrome c oxidase subunit 7C, mitochondrial | 5.4 |
| COX7A2 | Cytochrome c oxidase subunit 7A2, mitochondrial | 5.34 |
| SDHB | Succinate dehydrogenase iron-sulfur subunit, mitochondrial | 4.86 |
| COX5B | Cytochrome c oxidase subunit 5B, mitochondrial | 4.83 |
| CKMT2 | Creatine kinase S-type, mitochondrial | 4.78 |
| COQ6 | Ubiquinone biosynthesis monooxygenase COQ6, mitochondrial | 4.71 |
| HYOU1 | Hypoxia up-regulated protein 1 | 4.55 |
| CHDH | Choline dehydrogenase, mitochondrial | 4.42 |
| NDUFV1 | NADH dehydrogenase [ubiquinone] flavoprotein 1, mitochondrial | 4.31 |
| PUS1 | tRNA pseudouridine synthase A, mitochondrial | 4.28 |
| OXCT1 | Succinyl-CoA:3-ketoacid coenzyme A transferase 1, mitochondrial | 4.17 |
| TOMM6 | Mitochondrial import receptor subunit TOM6 | 4.15 |
| ACAA2 | 3-ketoacyl-CoA thiolase, mitochondrial | 4.04 |
| NFU1 | NFU1 iron-sulfur cluster scaffold homolog, mitochondrial | 3.96 |
| CPT1A | Carnitine O-palmitoyltransferase 1, liver isoform | 3.52 |
| UQCRC1 | Cytochrome b-c1 complex subunit 1, mitochondrial | 3.51 |
| PRKDC | DNA-dependent protein kinase catalytic subunit | 3.43 |
| MDH2 | Malate dehydrogenase, mitochondrial | 3.3 |
| ACSF3 | Acyl-CoA synthetase family member 3, mitochondrial | 3.29 |
| FH | Fumarate hydratase, mitochondrial | 3.27 |
| PDHX | Pyruvate dehydrogenase protein X component, mitochondrial | 3.23 |
| BDH1 | D-beta-hydroxybutyrate dehydrogenase, mitochondrial | 3.16 |
| NDUFS3 | NADH dehydrogenase iron-sulfur protein 3, mitochondrial | 3.16 |
| MMAB | Cob(I)yrinic acid a,c-diamide adenosyltransferase, mitochondrial | 3.12 |
| DARS2 | Aspartate--tRNA ligase, mitochondrial | 3 |

TABLE 1-continued

Key Mitochondrial-Related Proteins are Down-Regulated in Doxy-Resistant MCF7 Cells.

| Symbol | Description | Fold-reduction (Down-regulation) |
|---|---|---|
| SUCLA2 | Succinyl-CoA ligase [ADP-forming] subunit beta, mitochondrial | 2.91 |
| ABAT | 4-aminobutyrate aminotransferase, mitochondrial | 2.83 |
| LACTB | Serine beta-lactamase-like protein LACTB, mitochondrial | 2.81 |
| CHDH | Choline dehydrogenase, mitochondrial | 2.78 |
| GLS | Glutaminase kidney isoform, mitochondrial | 2.77 |
| TOMM34 | Mitochondrial import receptor subunit TOM34 | 2.76 |
| NDUFA10 | NADH dehydrogenase 1 alpha subcomplex subunit 10, mitochondrial | 2.7 |
| MUL1 | Mitochondrial ubiquitin ligase activator of NFKB 1 | 2.6 |
| UQCRC2 | Cytochrome b-c1 complex subunit 2, mitochondrial | 2.54 |
| COX7A2L | Cytochrome c oxidase subunit 7A-related protein, mitochondrial | 2.54 |
| SLC25A24 | Calcium-binding mitochondrial carrier protein SCaMC-1 | 2.51 |
| NDUFA9 | NADH dehydrogenase 1 alpha subcomplex subunit 9, mitochondrial | 2.5 |
| GLUL | Glutamine synthetase | 2.5 |
| PDHA1 | Pyruvate dehydrogenase E1 subunit alpha, somatic, mitochondrial | 2.5 |
| SDHA | Succinate dehydrogenase flavoprotein subunit, mitochondrial | 2.48 |
| NDUFS8 | NADH dehydrogenase iron-sulfur protein 8, mitochondrial | 2.42 |

Table 1 summarizes mitochondrial-related proteins that are down-regulated in MCF7-DoxyR cells. Down-regulated proteins include those encoded by mitochondrial DNA (mt-DNA) and nuclear DNA (nuc-DNA). For example, the cellular levels of MT-ND3, MT-CO2, MT-ATP6, and MT-ATP8 are reduced 5-35 fold. Such reductions may inactivate or impair the functioning of Complex I, IV, and V. Similarly, more than 45 nuclear-encoded mitochondrial proteins, such as NDUFS1, NDUFB8, and COX7C, are reduced between 2-12 fold. Loss of mt-DNA-encoded proteins is characteristic of the inhibition of mitochondrial protein translation.

In contrast, the levels of glycolytic enzymes, such as PGM1, LDHA, ALDOC, and GAPDH, increased 2-7 fold, as is shown in Table 2. Similarly, enzymes associated with glycogen metabolism increased 3-4 fold (Table 2).

TABLE 2

Enzymes Related to Glycolysis and Glycogen Metabolism are Up-Regulated in Doxy-Resistant MCF7 Cells.

| Symbol | Description | Fold-Increase (Up-regulation) |
|---|---|---|
| Glycolytic enzymes | | |
| PGM1 | Phosphoglucomutase-1 | 7.16 |
| LDHA | L-lactate dehydrogenase A | 7.09 |
| ALDOC | Fructose-bisphosphate aldolase C | 3.44 |
| GAPDH | Glyceraldehyde-3-phosphate dehydrogenase | 3.06 |
| GPD1L | Glycerol-3-phosphate dehydrogenase 1-like protein | 2.72 |
| ALDOA | Fructose-bisphosphate aldolase A | 2.71 |
| PFKP | ATP-dependent 6-phosphofructokinase, platelet type | 2.69 |
| PGK1 | Phosphoglycerate kinase 1 | 2.64 |
| GPI | Glucose-6-phosphate isomerase | 2.46 |
| PKM | Pyruvate kinase | 2.1 |
| Glycogen metabolism | | |
| GYS1 | Glycogen [starch] synthase, muscle | 4.11 |
| PYGM | Glycogen phosphorylase, muscle form | 3.45 |
| PYGL | Glycogen phosphorylase, liver form | 3.39 |

Table 3 shows that markers of hypoxia, including myoglobin and hemoglobin (alpha/delta), were elevated, thus further suggesting a predominantly glycolytic phenotype. Consistent with an increase in Aldefluor activity, several ALDH gene products were increased, such as ALDH1A3. Increased ALDH activity may reflect the cells' preference towards glycolysis, as ALDH isoforms contribute significantly to the glycolytic pathway.

TABLE 3

Markers of Hypoxia and Cancer Stem Cells are Up-regulated in Doxy-Resistant MCF7 Cells.

| Symbol | Description | Fold-Increase (up-regulation) |
|---|---|---|
| Hypoxia markers | | |
| MB | Myoglobin | 5.86 |
| HBA1 | Hemoglobin subunit alpha | 3.46 |
| HBD | Hemoglobin subunit delta | 1.81 |
| ALDH gene isoforms | | |
| ALDH1A3 | Aldehyde dehydrogenase family 1 member A3 | 1,681.32 |
| ALDH1A2 | Retinal dehydrogenase 2 | 5.22 |
| ALDH5A1 | Succinate-semialdehyde dehydrogenase, mitochondrial | 3.87 |
| ALDH18A1 | Delta-1-pyrroline-5-carboxylate synthase | 2.75 |
| ALDH16A1 | Aldehyde dehydrogenase family 16 member A1 | 2.04 |
| Other cancer stem cell (CSC) markers | | |
| RGAP2 | SLIT-ROBO Rho GTPase-activating protein 2 | 2.8 |
| CD44 | CD44 antigen | 2.09 |

Table 4 shows that ten mitochondrial ribosomal proteins (MRPs) increased between 1.5-3 fold. Increases in MRPs may explain the increase in the mitochondrial mass discussed above and in FIG. 2.

TABLE 4

A Subset of Mitochondrial Ribosomal Proteins (MRPs) are Increased in Doxy-Resistant MCF7 Cells.

| Symbol | Description | Fold-Increase (up-regulation) |
|---|---|---|
| Small subunit | | |
| MRPS25 | 28S ribosomal protein S25, mitochondrial | 3.02 |
| MRPS9 | 28S ribosomal protein S9, mitochondrial | 1.69 |
| MRPS18C | 28S ribosomal protein S18c, mitochondrial | 1.58 |

TABLE 4-continued

A Subset of Mitochondrial Ribosomal Proteins (MRPs) are Increased in Doxy-Resistant MCF7 Cells.

| Symbol | Description | Fold-Increase (up-regulation) |
|---|---|---|
| Large subunit | | |
| MRPL10 | 39S ribosomal protein L10, mitochondrial | 2.9 |
| MRPL12 | 39S ribosomal protein L12, mitochondrial | 2.21 |
| MRPL46 | 39S ribosomal protein L46, mitochondrial | 2.13 |
| MRPL53 | 39S ribosomal protein L53, mitochondrial | 2.13 |
| MRPL37 | 39S ribosomal protein L37, mitochondrial | 2.05 |
| MRPL19 | 39S ribosomal protein L19, mitochondrial | 1.95 |
| MRPL15 | 39S ribosomal protein L15, mitochondrial | 1.94 |

Table 5 illustrates that cellular ribosomal proteins may be down-regulated, between 1.8-9 fold. Such downregulation may drive decreases in cellular protein synthesis due to mitochondrial energy deficits, resulting in a quiescent metabolic phenotype.

TABLE 5

A Subset of Cellular Ribosomal Proteins are Decreased in Doxy-Resistant MCF7 Cells.

| Symbol | Description | Fold-reduction (Down-regulation) |
|---|---|---|
| Small subunit | | |
| RPS15 | 40S ribosomal protein S15 | 2.12 |
| RPS21 | 40S ribosomal protein S21 | 2.08 |
| RPS4X | 40S ribosomal protein S4, X isoform | 2.06 |
| RPS23 | 40S ribosomal protein S23 | 1.82 |
| Large subunit | | |
| RPL34 | 60S ribosomal protein L34 | 9.85 |
| RPL3 | 60S ribosomal protein L3 | 6.39 |
| RPLP2 | 60S acidic ribosomal protein P2 | 3.68 |
| RPL10A | 60S ribosomal protein L10a | 2.28 |
| RPL27A | 60S ribosomal protein L27a | 2.06 |
| RPL8 | 60S ribosomal protein L8 | 1.93 |
| RPL22L1 | 60S ribosomal protein L22-like 1 | 1.82 |
| Other | | |
| RSL1D1 | Ribosomal L1 domain-containing protein 1 | 3.08 |

Figure 8:
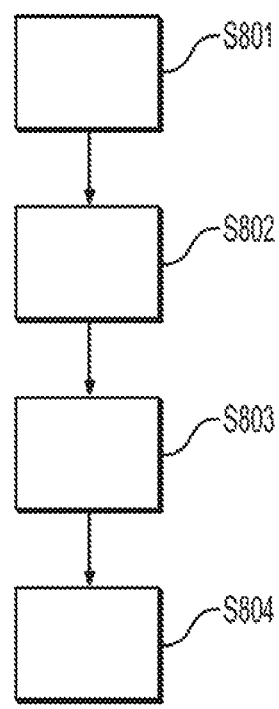
FIG. 8 outlines a method for targeting mitochondrial activity and glycolysis to target and eradicate CSCs.

The DoxyR cells acquire a predominantly glycolytic phenotype to escape the anti-mitochondrial effects of doxycycline. The inventors hypothesized that the DoxyR cells are metabolically synchronized, are metabolically inflexible, and therefore should be sensitive to additional metabolic stressors or perturbations, allowing them to be eliminated completely. The inventors hypothesized that additional metabolic stressors could be added using metabolic inhibitors targeting glycolysis, OXPHOS, and/or autophagy. This "two-hit" metabolic scheme is illustrated in FIG. 8. DoxyR cells are identified S801, and are characterized as metabolically synchronized and metabolically inflexible S802. DoxyR cells may be exposed to one or more metabolic stressor, such as metabolic inhibitors targeting glycolysis, OXPHOS, and/or autophagy, thereby reducing doxycycline resistance S803. Then doxycycline (or another antimitochondrial compound) may be administered to eradicate the cells during their reduced resistance S804.

To test the "two-hit" metabolic hypothesis, the inventors tested the effects of Atovaquone, an FDA-approved OXPHOS inhibitor which targets mitochondrial Complex III, and Chloroquine, an autophagy inhibitor. Atovaquone and Chloroquine are normally used clinically for the treatment and prevention of malaria, a parasitic infection. It should be appreciated by one of skill in the art that other OXPHOS and autophagy inhibitors may be selected. A list of exemplary metabolic inhibitors is presented below.

TABLE 6

Combination Therapies

| Doxycycline Plus OXPHOS Inhibitor | Doxycycline Plus Glycolysis Inhibitor | Doxycycline Plus Autophagy Inhibitor |
|---|---|---|
| Atovaquone | 2-Deoxy-glucose (2-DG) | Chloroquine |
| Irinotecan | Ascorbic acid | |
| Sorafenib | Stiripentol | |
| Niclosamide | | |
| Berberine Chloride | | |

Figure 9:
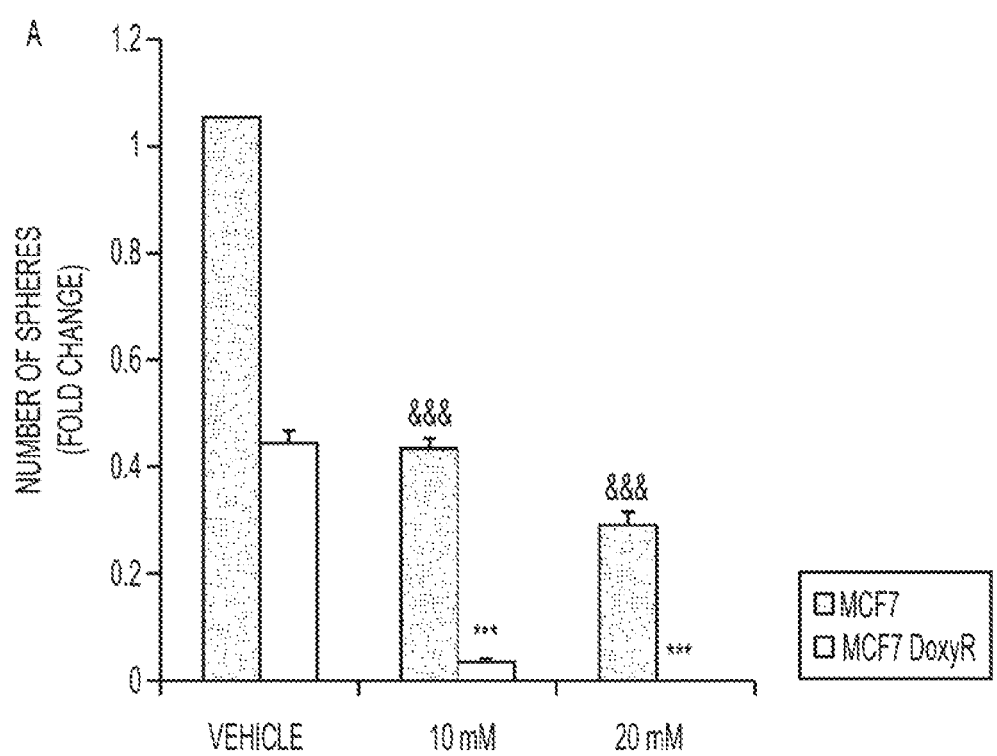
FIGS. 9 and 10 show the effects of glycolysis inhibitors 2-deoxy-glucose (2 DG) (FIG. 9) and ascorbic acid (FIG. 10) on mammosphere formation in doxycycline-treated MCF7 cells.
Figure 10:
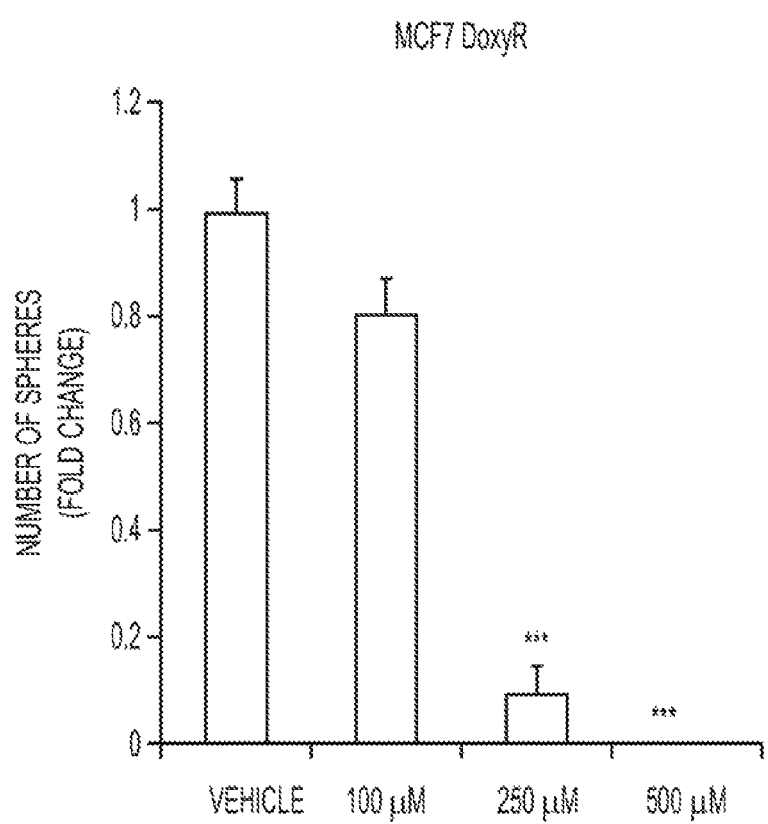
Figure 11A:
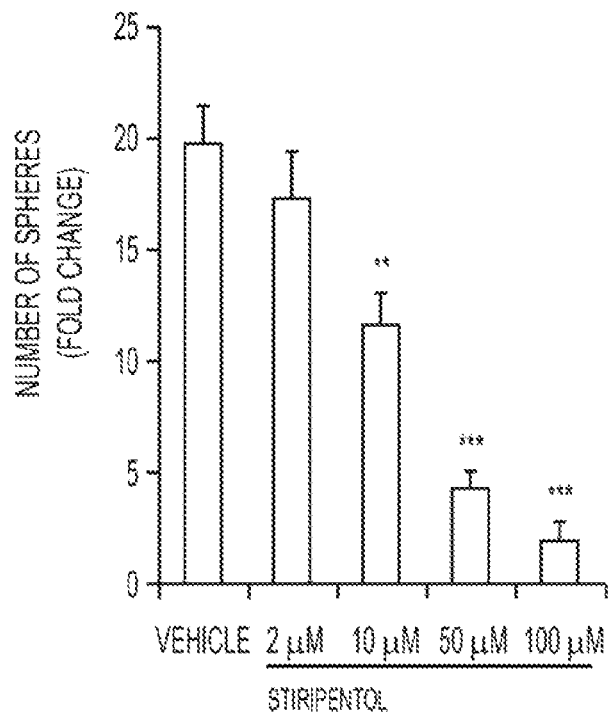
FIGS. 11A-F show the effects of Stiripentol (FIG. 11A), Irinotecan (FIG. 11B), Sorafenib (FIG. 11C), Berberine Chloride (FIG. 11D), and Niclosamide (FIG. 11E-F) on mammosphere formation in doxycycline-treated MCF7 cells.
Figure 11B:
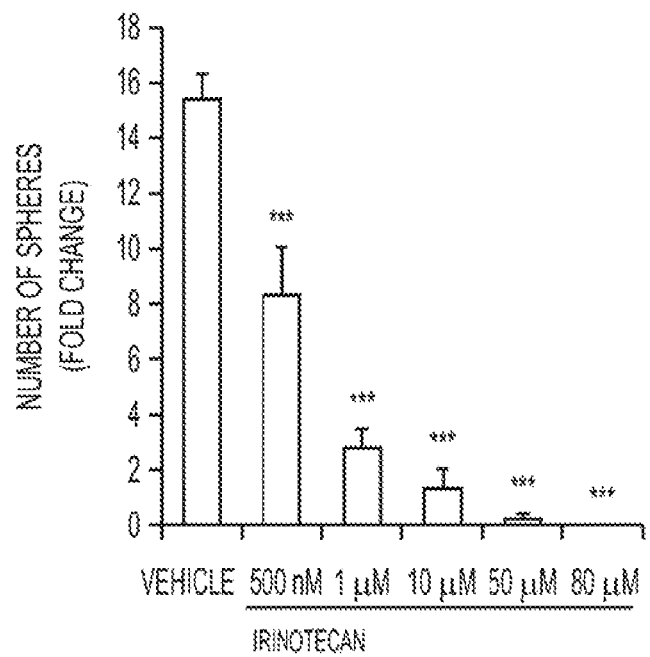
Figure 11C:
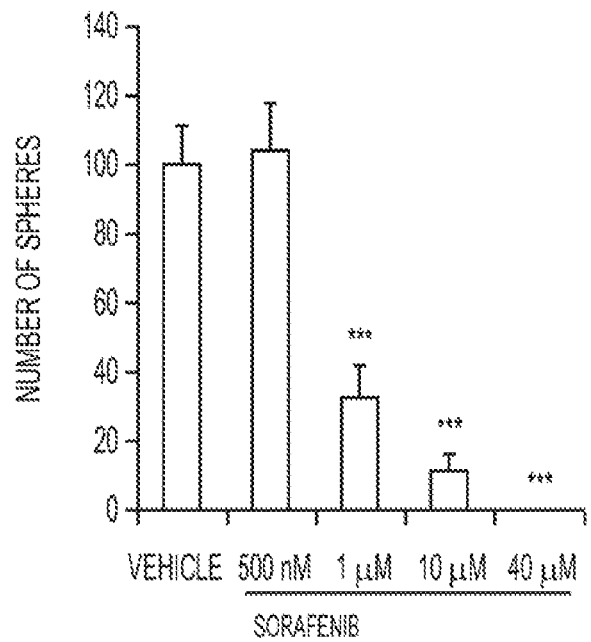
Figure 11D:
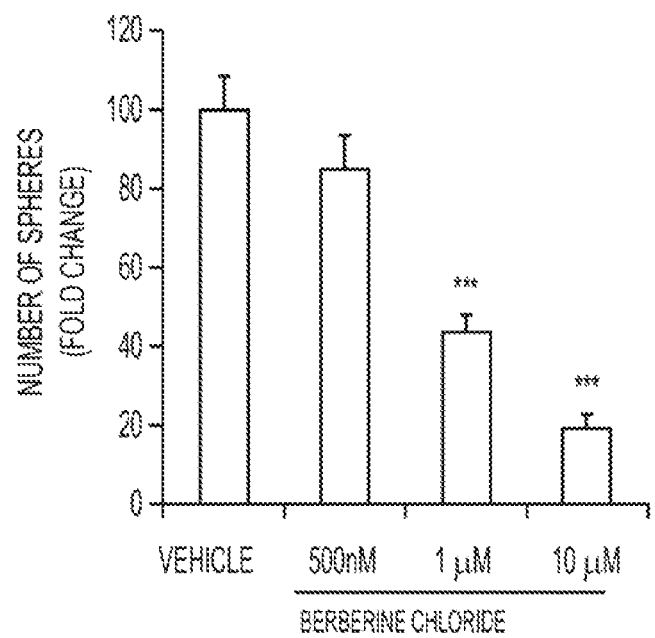
Figure 11E:
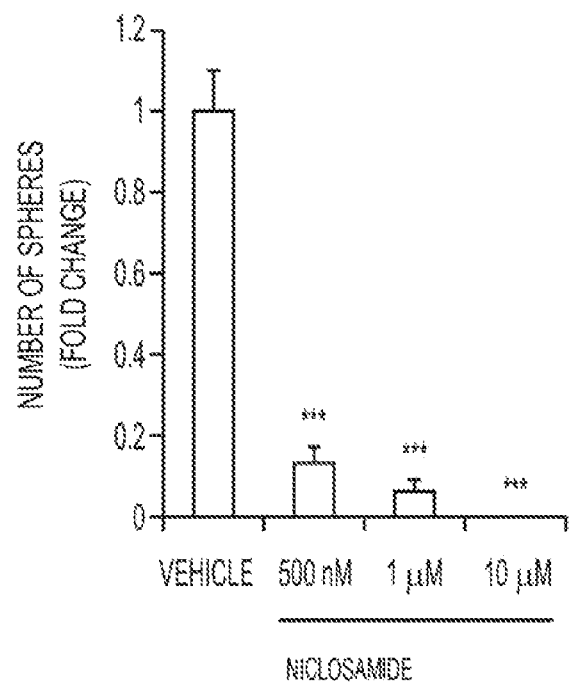
Figure 11F:
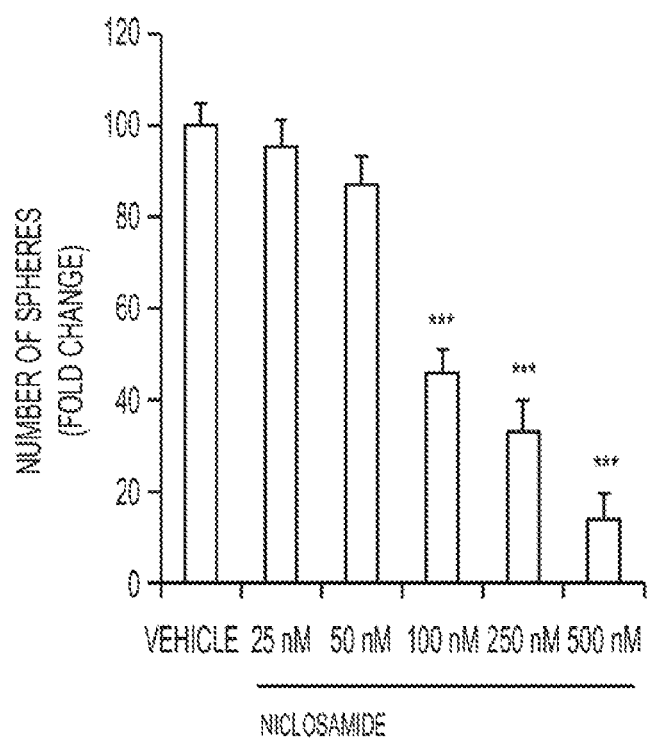
Figure 12:
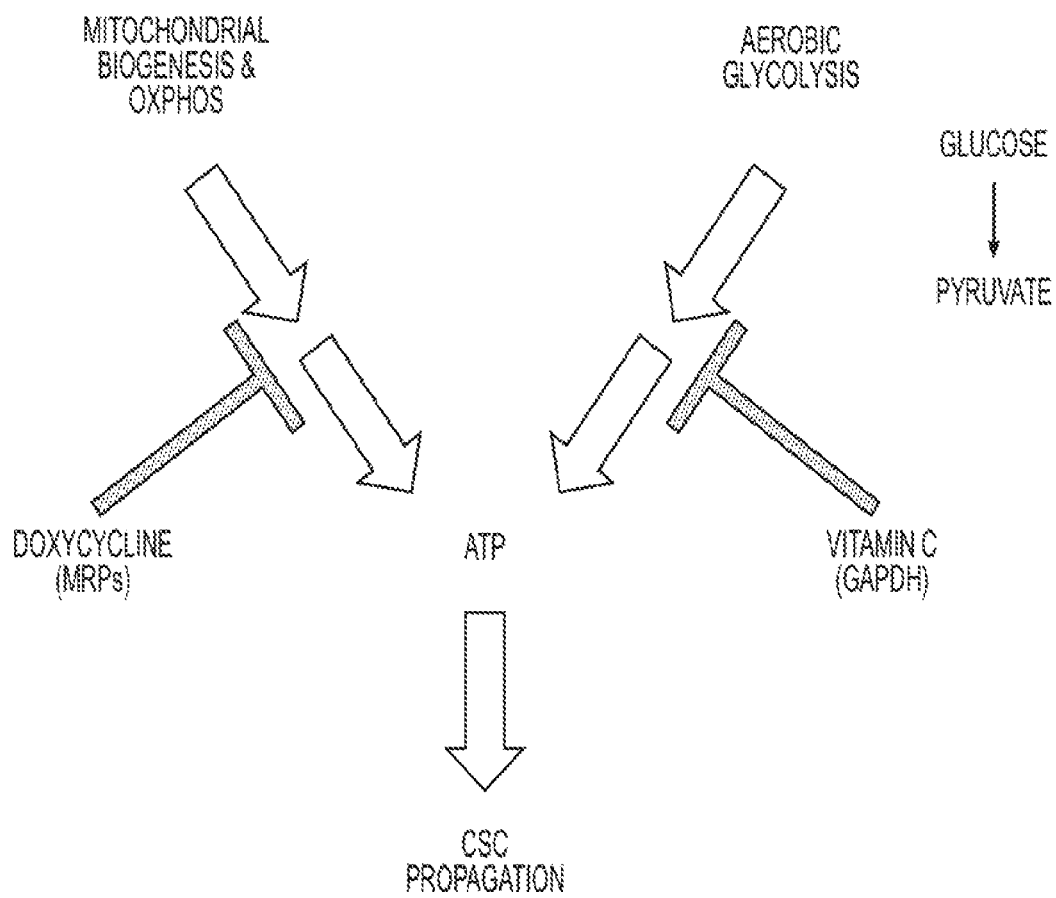
FIG. 12 outlines the method by which mitochondrial function and glycolysis are blocked to inhibit CSC propagation.

The present approach further involves methods of testing the efficacy of glycolysis inhibitors on CSC propagation using 2-deoxy-glucose (2-DG) and Vitamin C (ascorbic acid). It should be appreciated that other glycolysis inhibitors may be used. Treatment with 2-DG inhibited the propagation of DoxyR CSCs by more than 90% at 10 mM and 100% at 20 mM (FIGS. 9 and 10). Vitamin C may be more potent than 2-DG, as it inhibited DoxyR CSC propagation by more than 90% at 250 μM and 100% at 500 μM (FIGS. 9 and 10). The IC-50 for Vitamin C in this experiment was between 100 to 250 μM, which is within the known achievable blood levels when Vitamin C is taken orally. The inventors previously showed that the IC-50 for Vitamin C was 1 mM for MCF7 CSC propagation. Bonuccelli et al, *Oncotarget* 8:20667-20678 (2017). Therefore, DoxyR CSCs may be approximately 4-10-fold more sensitive to Vitamin C than control MCF7 CSCs under identical assay conditions.

The present approach further involves methods of testing the efficacy of glycolysis inhibitors on CSC propagation using other clinically-approved drugs that functionally behave as OXPHOS inhibitors (Irinotecan, Sorafenib, Niclosamide) or glycolysis inhibitors (Stiripentol) on mammosphere formation. Briefly, MCF7 DoxyR cells were cultured in low attachment plates and treated with Vehicle or increasing concentrations of the lactate dehydrogenase (LDH) inhibitor Stiripentol (2 μM to 100 μM) (FIG. 11A) or the OXPHOS inhibitors Irinotecan (500 nM to 80 μM) (FIG. 11B), Sorafenib (500 nM to 40 μM) (FIG. 11C), Berberine Chloride (500 nM to 10 μM) (FIG. 11D) and Niclosamide (FIG. 11E-F) for 5 days before counting. Independent experiments were performed in triplicate. FIG. 11A-F shows that Niclosamide was most potent at inhibiting DoxyR CSC propagation (IC-50 ~100 nM), followed by Irinotecan (IC-50 ~500 nM), Sorafenib (IC-50 ~0.5-1 μM), Berberine (IC-50 ~1 μM) and Stiripentol (IC-50 ~10-50 μM).

Mitochondrial biogenesis inhibitors include tetracyclines (e.g., tetracycline, doxycycline, tigecycline, and minocycline); erythromycins (e.g., eyrthromycin, azithromycin, and clarithromycin); pyrvinium pamoate; atovaquone; bedaquiline; irinotecan; sorafenib; niclosamide; berberine; stiripentol; chloroquine; etomoxir; perhexiline; mitoriboscins, such as those disclosed in U.S. Provisional Patent Application No. 62/471,688, filed Mar. 15, 2017, and Patent Cooperation Treaty (PCT) Patent Application PCT/US2018/022403, filed Mar. 14, 2018, the entireties of which are incorporated herein by reference; mitoketoscins, such as those disclosed in U.S. Provisional Patent Application No. 62/524,829, filed Jun. 26, 2017, the entirety of which is incorporated herein by reference; mitoflavoscins, such as those disclosed in U.S. Provisional Patent Application No. 62/576,287, filed Oct. 24, 2017, the entirety of which is incorporated herein by reference; TPP-compounds (e.g., 2-butene-1,4-bis-TPP), such as those disclosed in U.S. Provisional Patent Application No. 62/590,432, filed Nov. 24, 2017, the entirety of which is incorporated herein by reference; mDIVI1, such as those disclosed in U.S. Provisional Patent Application No. 62/608,065, filed Dec. 20, 2017, the entirety of which is incorporated herein by reference; CAPE (caffeic acid phenyl ester); antimitoscins, such as those disclosed in 62/508,702, filed May 19, 2017, the entirety of which is incorporated herein by reference; repurposcins such as those disclosed in U.S. Provisional Patent Application No. 62/593,372, filed Dec. 1, 2017, the entirety of which is incorporated herein by reference; other known mitochondrial inhibitors.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise. The invention includes numerous alternatives, modifications, and equivalents as will become apparent from consideration of the following detailed description.

It will be understood that although the terms "first," "second," "third," "a)," "b)," and "c)," etc. may be used herein to describe various elements of the invention should not be limited by these terms. These terms are only used to distinguish one element of the invention from another. Thus, a first element discussed below could be termed a element aspect, and similarly, a third without departing from the teachings of the present invention. Thus, the terms "first," "second," "third," "a)," "b)," and "c)," etc. are not intended to necessarily convey a sequence or other hierarchy to the associated elements but are used for identification purposes only. The sequence of operations (or steps) is not limited to the order presented in the claims.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. Thus, the term consisting essentially of" as used herein should not be interpreted as equivalent to "comprising."

The term "about," as used herein when referring to a measurable value, such as, for example, an amount or concentration and the like, is meant to encompass variations of ±20%, ±10%, ±5%, ±1%, ±0.5%, or even ±0.1% of the specified amount. A range provided herein for a measureable value may include any other range and/or individual value therein.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

What is claimed is:

1. A method of treating cancer comprising administering to a patient in need thereof a pharmaceutically effective amount of doxycycline and an inhibitor of glycolytic metabolism is ascorbic acid.

2. The method of claim 1, wherein the inhibitor of glycolytic metabolism is ascorbic acid, and the concentration of ascorbic acid is sufficient to achieve an ascorbic acid blood concentration between 250 μM and 500 μM.

3. The method of claim 1, wherein the cancer to be treated comprises cancer stem cells having a resistance to doxycycline.

4. The method of claim 1, wherein the wherein the cancer to be treated comprises breast cancer.

5. The method of claim 4, wherein the breast cancer comprises cancer stem cells having a resistance to doxycycline.

6. The method of claim 3, further comprising reducing the doxycycline resistance through administration of the inhibitor of glycolytic metabolism prior to administering doxycycline.

* * * * *